(12) United States Patent
Chu et al.

(10) Patent No.: US 8,058,403 B2
(45) Date of Patent: Nov. 15, 2011

(54) ANTIBODIES TO STROMAL CELL-DERIVED FACTOR-1 POLYPEPTIDES

(75) Inventors: Keting Chu, Hillsborough, CA (US); Lewis T. Williams, Mill Valley, CA (US); Justin G. P. Wong, Oakland, CA (US); Kevin Hestir, Kensington, CA (US); Amy L. Tsui Collins, Oakland, CA (US); Ernestine Lee, Kensington, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 12/752,936

(22) Filed: Apr. 1, 2010

(65) Prior Publication Data

US 2011/0020375 A1    Jan. 27, 2011

Related U.S. Application Data

(62) Division of application No. 11/587,651, filed as application No. PCT/US2005/014963 on Apr. 29, 2005, now Pat. No. 7,776,564.

(60) Provisional application No. 60/567,311, filed on Apr. 30, 2004.

(51) Int. Cl.
*C07K 16/24* (2006.01)
(52) U.S. Cl. ............... 530/387.9; 530/387.3; 530/388.1; 530/388.15
(58) Field of Classification Search .................. None
See application file for complete search history.

(56) References Cited

U.S. PATENT DOCUMENTS

| | | | | |
|---|---|---|---|---|
| 5,011,912 | A | * | 4/1991 | Hopp et al. ............... 530/387.9 |
| 5,169,939 | A | * | 12/1992 | Gefter et al. ............... 530/387.3 |
| 5,492,841 | A | * | 2/1996 | Craig ............................ 436/534 |
| 5,530,101 | A | * | 6/1996 | Queen et al. ............... 530/387.3 |
| 5,601,819 | A | * | 2/1997 | Wong et al. ................. 424/136.1 |
| 6,214,540 | B1 | | 4/2001 | DeVico et al. |
| 6,428,970 | B2 | | 8/2002 | De Vico et al. |
| 6,613,742 | B1 | | 9/2003 | Huang et al. |
| 2002/0107195 | A1 | | 8/2002 | Gupta |
| 2003/0215792 | A1 | | 11/2003 | Muller et al. |

FOREIGN PATENT DOCUMENTS

| | | |
|---|---|---|
| EP | 1 072 273 A1 | 1/2001 |
| WO | WO 99/29728 A1 | 6/1999 |
| WO | WO 00/06086 A2 | 2/2000 |
| WO | WO 01/92530 A1 | 12/2001 |

OTHER PUBLICATIONS

Nishimura et al., "Molecular Cloning and Sequencing of Feline Stromal Cell-derived Factor 1-α and β," *European Journal of Immunogenetics*, 25(4): 303-305 (1998).
Tang et al., "Hypoxic Preconditioning Enhances the Benefit of Cardiac Progenitor Cell Therapy for Treatment of Myocardial Infarction by Inducing CXCR4 Expression," *Circulation Research*, 104: 1209-1216 (2009).
Yu et al., "Identification and Expression of Novel Isoforms of Human Stromal Cell-derived Factor 1," *Gene*, 374: 174-179 (2006).
U.S. Appl. No. 11/587,651, filed Jun. 30, 2008.

\* cited by examiner

*Primary Examiner* — Prema Mertz
(74) *Attorney, Agent, or Firm* — Finnegan, Henderson, Farabowm Garrett and Dunner, LLP

(57) ABSTRACT

Disclosed herein is a newly identified SDF-1 splice variant molecule, its polypeptide sequence, and the polynucleotides encoding the polypeptide sequence, and active fragments thereof. Also provided is a procedure for producing such polypeptides by recombinant techniques employing, for example, vectors and host cells. Also disclosed are methods for utilizing such polypeptides and modulators thereof for the treatment of diseases, including cancer, immune diseases, infectious diseases, and ischemic diseases.

9 Claims, 1 Drawing Sheet

```
CLN00235738_5pv1.a          MNAKVVVVLVLVLTALCLSDGKPVSLSYRCPCRFFESHVARANVKHLKILNTPNCALQIV 60
CLN00235738_5pv1.a_exon2-4  --------------------KPVSLSYRCPCRFFESHVARANVKHLKILNTPNCALQIV 39
CLN00235738_5pv1.a_exon3-4  ------------------------------------------------------------ 0
1220364_1220363             MNAKVVVVLVLVLTALCLSDGKPVSLSYRCPCRFFESHVARANVKHLKILNTPNCALQIV 60
10334450_1220365            MNAKVVVVLVLVLTALCLSDGKPVSLSYRCPCRFFESHVARANVKHLKILNTPNCALQIV 60
NP_000600_NM_000609         MNAKVVVVLVLVLTALCLSDGKPVSLSYRCPCRFFESHVARANVKHLKILNTPNCALQIV 60
18093693                    MNAKVVVVLVLVLTALCLSDGKPVSLSYRCPCRFFESHVARANVKHLKILNTPNCALQIV 60
CLN00235738_5pv1.a_exon4    ------------------------------------------------------------ 0
CLN00235738_5pv1.a_3p_region ----------------------------------------------------------- 0

CLN00235738_5pv1.a          ARLKNNNRQVCIDPKLKWIQEYLEKALNNLISAAPAGKRVIAGARALHPSPPRACPTARA
120
CLN00235738_5pv1.a_exon2-4  ARLKNNNRQVCIDPKLKWIQEYLEKALNNLISAAPAGKRVIAGARALHPSPPRACPTARA 99
CLN00235738_5pv1.a_exon3-4  ARLKNNNRQVCIDPKLKWIQEYLEKALNNLISAAPAGKRVIAGARALHPSPPRACPTARA 60
1220364_1220363             ARLKNNNRQVCIDPKLKWIQEYLEKALNK------------------------------ 89
10334450_1220365            ARLKNNNRQVCIDPKLKWIQEYLEKALNKFKM--------------------------- 92
NP_000600_NM_000609         ARLKNNNRQVCIDPKLKWIQEYLEKALNKRFKM-------------------------- 93
18093693                    ARLKNNNRQVCIDPKLKWIQEYLEKALNKGRREEKVGKKEKIGKKKRQKKRKAAQKRKN-
119
CLN00235738_5pv1.a_exon4    ----------------------------LISAAPAGKRVIAGARALHPSPPRACPTARA 31
CLN00235738_5pv1.a_3p_region ----------------------------------------------------------A 1

CLN00235738_5pv1.a          LCEIRLWPPPEWSWPSPGDV 140
CLN00235738_5pv1.a_exon2-4  LCEIRLWPPPEWSWPSPGDV 119
CLN00235738_5pv1.a_exon3-4  LCEIRLWPPPEWSWPSPGDV 80
1220364_1220363             -------------------- 89
10334450_1220365            -------------------- 92
NP_000600_NM_000609         -------------------- 93
18093693                    -------------------- 119
CLN00235738_5pv1.a_exon4    LCEIRLWPPPEWSWPSPGDV 51
CLN00235738_5pv1.a_3p_region LCEIRLWPPPEWSWPSPGDV 21
```

Figure 1

ANTIBODIES TO STROMAL CELL-DERIVED FACTOR-1 POLYPEPTIDES

PRIORITY CLAIM

This application is a divisional of U.S. patent application Ser. No. 11/587,651, now U.S. Pat. No. 7,776,564, which is a §371 national phase filing of International Application No. PCT/US05/14963, filed Apr. 29, 2005, which claims the benefit of U.S. Provisional Application No. 60/567,311, filed Apr. 30, 2004, the disclosures of all of which are hereby incorporated by reference in their entireties.

TECHNICAL FIELD

The present invention relates to newly identified stromal cell-derived factor-1 ("SDF-1") polypeptides, polynucleotides encoding such, modulators thereof, vectors, host cells, compositions, and kits containing such, the methods of making and methods of using such polypeptides, polynucleotides, and modulators, such as antibodies, in diagnostic, prophylactic, and therapeutic applications.

BACKGROUND OF THE INVENTION

Chemokines, or chemotactic cytokines, are a class of cytokine molecules capable of chemotactically attracting migratory cells. Chemokines are essential in attracting cells to inflammatory sites irrespective of the etiology, including immunologic, infective, ischemic, or drug-induced causes of inflammation. Chemokines generally are small molecular weight molecules in the range of about 8-10 kilodaltons ("kD").

Most chemokines can be divided into three major families, CC, CXC, and CXXXC, based on the number of amino acids (referred to as "X") separating the two cysteines (referred to as "C") in the chemokine molecule. Within the CC and CXC families, chemokines are further grouped into related sub-families based on amino acid sequence similarity. CC chemokine sub-families include the monocyte chemoattractant protein ("MCP") sub-family and the sub-families that include macrophage inhibitory protein-1α ("MIP-1α"), macrophage inhibitory protein-1β ("MIP-1β"), and the regulated on activation normal T cell expressed ("RANTES") subfamily. CXC chemokine sub-families include the T-10 and Mig sub-family, the interleukin-8 ("IL-8") sub-family, and the PF4 sub-family. The chemokines stromal cell-derived factor 1α ("SDF-1α") and stromal cell-derived factor 1β ("SDF-1β") form a chemokine family that is related by amino acid sequence similarity to the both CC and CXC chemokine families.

Chemokines generally exert their effect by binding to chemokine receptors. CC chemokines typically bind to members of the CCR class of receptors, while CXC chemokines typically bind to members of the CXCR class of receptors. These receptors are involved in regulating the extent and nature of inflammation, and certain receptors tend to be localized in certain tissues and cells.

Stromal cell-derived factor-1 ("SDF-1"), a member of the CXC chemokine family, is a potent chemoattractant for hematopoietic cells, including bone marrow progenitors (Aiuti et al., *J. Exp. Med.*, 185:111-120 (1991)), lymphocytes (Bleul et al., *Nature* (Lond.), 382:828-833 (1996)), monocytes, and polymorphonuclear cells (Bleul et al., *J. Exp. Med.*, 184:1101-1109 (1996)). SDF-1 also stimulates proliferation of β-cell progenitors in vitro (Nagasawa et al., *Nature* (Lond.), 382:635-638 (1996)). SDF-1 is thus likely to attract hematopoietic cells in appropriate microenvironments in which they differentiate or proliferate in response to local stimuli. SDF-1 is the ligand for CXCR4, a G protein-coupled receptor that is expressed not only in hematopoietic cells but also in a large variety of tissues, such as brain microglia (Lavi et al., *Am. J. Pathol.*, 1035-1042 (1997)), and endothelia (Gupta et al., *J. Biol. Chem.*, 273:4282-4287 (1998)). Accordingly, CXCR4-deficient mice exhibited cardiac defects, abnormal cerebellar development, and anatomical changes of gastrointestinal tract vascularization (Tachibana et al., *Nature* (Lond.), 393:591-594 (1998)).

SDF-1 is believed to play an important role during embryogenesis and hematopoeisis by recruiting hematopoietic stem cell ("HSC") precursors to become bone marrow cells. In the adult, SDF-1 is hypothesized to be involved in migration of lymphocytes to lymphoid organs or to sites of inflammation. SDF-1 is expressed in both splenic red pulp and in lymph node medullary cords, as well as on high endothelial venules ("HEV"). Moreover, SDF-1 has been found to induce recruitment of an SDF-1 responsive cell line to human peripheral lymph nodes grafted into SCID mice. However, the entire role of SDF-1 in health and disease is not yet clear.

BRIEF DESCRIPTION OF THE FIGURES AND TABLES

Brief Description of the Figure

FIG. 1 shows the polypeptide alignment of SEQ. ID. NOS.: 9-13. SEQ. ID. NO.:9 is the novel SDF-1 polypeptide of the invention. SEQ. ID. NOS.:10-13 are known sequences from the NCBI database. SEQ. ID. NOS.:14-16 are active fragments of the novel SDF-1 polypeptide, containing exons 2-4, exons 3-4, and exon 4 respectively. SEQ. ID. NO.:22 is the 3' region from SEQ. ID. NO.:9, which contains the region not shown in the public sequence SEQ. ID. NO.:12. SEQ. ID. NO.:23 is the 5' region from SEQ. ID. NO.:9. The alignment was performed using Clustal Format for T-COFFEE Version_1.37, CPU=0.00 sec, SCORE=76, Nseq=9, Len=140. Table 1 shows the correlation between SEQ. ID NOS. and the sequences as designated in FIG. 1.

BRIEF DESCRIPTION OF THE TABLES

In Table 1, column 1 shows an internal designation identification number (FP ID); column 2 shows the nucleotide sequence identification number for the open reading frame of the nucleic acid sequence (SEQ. ID. NO.:N1); column 3 shows the amino acid sequence identification number for the polypeptide sequence (SEQ. ID. NO.:P1); column 4 shows the nucleotide sequence identification number for the entire nucleic acid sequence (SEQ. ID. NO.:N0); and column 5 shows the polypeptide identification number of the source clone or sequence (Source ID).

Table 2 shows the public annotation of the polypeptide sequences of the Sequence Listing. Column 1 shows an internal designation identification number of the polypeptide (FY ID); column 2 shows the source identification number of the polypeptide (Source ID); column 3 shows the predicted length of the polypeptide (Pred Prot Len); column 4 shows the public ID number of a best human hit found in the NCBI public database NR (Top Human Hit Accession ID); column 5 shows the annotation of the ID number set forth in column 4 (Top Human Hit Annotation); column 6 comprises the top hit polypeptide length of the sequence set forth in column 4 (Top Human Hit % ID); and column 7 shows the length of the match between the polypeptide and the sequence shown in column 4 Top Human Match Length).

Table 3 shows information about the polypeptides of the Sequence Listing. Column 1 shows an internal designation identification number of the polypeptide (FP ID); column 2 shows the source identification number of the polypeptide (Source ID); column 3 shows the cluster identification number of the polypeptide (Cluster); column 4 shows the classification of the polypeptide (Class); column 5 shows the predicted protein length (Pred Prot Len); column 6 shows an internal parameter which designates whether a polypeptide is secreted; treevotes of 0.98 and 1 designate that the polypeptide is secreted and treevotes of 0.05-0.21 designate that the polypeptide is not secreted (Treevote); column 7 shows the mature protein coordinates (Mature Protein Coords); column 8 shows the signal peptide coordinates (Signal Peptide Coords); column 9 shows an alternate prediction of the mature protein coordinates (Alternate Mature Protein Coords); column 10 shows the number of transmembrane domains; coordinates of transmembrane domains (TM); and column 11 shows the protein family (Pfam).

Table 4 shows a comparison between the disclosed polypeptide and known variants. Column 1 shows an internal designation identification number of the polypeptide (FP ID); column 2 shows the source identification number of the polypeptide (Source ID); column 3 shows the predicted polypeptide length of the sequence shown in column 2 (Pred Prot Len); column 4 shows the length of the match between the disclosed polypeptide (FP ID) and the sequence shown in column 2 (Source ID); column 5 shows the percent identity between the disclosed polypeptide (FP ID) and the sequence shown in column 2 (Source ID); over the length of the disclosed polypeptide (FP ID); and column 6 shows the percent identity between the disclosed polypeptide (FP ID) and the sequence shown in column 2 (Source ID) over the length of the sequence shown in column 2 (Source ID).

Table 5 shows the Pfam coordinates of the invention. Column 1 shows an internal designation identification number of the polypeptide (FP ID); column 2 shows the source identification number of the polypeptide (Source ID); column 3 shows the name of the Pfam domain; and column 4 shows the start and stop coordinates of the pfam domain within the polypeptide.

INDUSTRIAL APPLICABILITY

The polypeptide and modulator compositions and methods of the invention are useful in the diagnosis, treatment, and/or prevention of proliferative diseases, inflammatory and immune or autoimmune diseases, hematopoeitic diseases, infectious diseases, ischemic diseases, and metabolic diseases. They are also useful in modulating an immune response and inhibiting tumor growth.

DISCLOSURE OF THE INVENTION

Summary of the Invention

The inventors herein have found novel SDF-1 polypeptides, polynucleotides encoding such, as well as modulators thereof that are useful in stimulating and inhibiting certain biological activities. The polypeptides of the present invention may be used for diseases relating to insufficient or abnormal proliferation of hematopoietic cells, neuronal enhancement or depression, and immunological enhancement and depression. For example, SDF-1 polypeptides, polynucleotides, and modulators thereof can be used for treatment or prevention of inflammatory diseases including rheumatoid arthritis and ulcerative colitis, hematopoietic stem cytopenia after bone marrow transplantation, leukocytopenia, thrombocytopenia, B lymphopenia and T lymphopenia after chemotherapy, anemia, infectious diseases, cancer, leukocytosis, HIV infection, neurodegenerative diseases including Alzheimer's disease and multiple sclerosis, neuronal injury, bone disorders such as osteoporosis, and/or tissue repair.

The present invention provides newly identified SDF-1 variant polypeptides, as well as isolated polynucleotides encoding the polypeptides and expression vectors containing the isolated polynucleotides. Accordingly, the invention provides methods and compositions for treatment, prevention, and diagnosis of diseases or conditions associated with the polypeptides of the invention, as well as the polynucleotides encoding the polypeptides.

The invention also provides a method for producing the disclosed polypeptides by cell free expression and culturing host cells transformed with a recombinant expression vector that contains the polypeptides encoding nucleic acids under conditions appropriate for expression of polypeptides, and recovering the expressed polypeptides from the culture.

The invention further provides modulators of the polypeptides of the invention, including but not limited to antibodies thereto, for treatment, prevention, and diagnosis of diseases or conditions associated with their respective receptors. Antibodies of the invention may specifically bind to or interfere with the activity of polypeptides of the invention, wherein such polypeptides contain at least a sequence of six contiguous amino acid residues chosen from the polypeptides of the Sequence Listing.

The invention yet further identifies further uses for the polypeptides of the invention, as well as the isolated polynucleotides encoding the polypeptides and modulators thereto.

In another aspect, the invention provides compositions containing the polypeptides of the invention, and a vehicle such as pharmaceutically acceptable carrier or excipient, wherein the compositions are useful for treatment or prophylaxis of diseases in animals.

The invention also provides a method for stimulating an immune response in a subject with the polypeptides of the invention and the isolated polynucleotides encoding the polypeptides of the invention.

The invention further provides a method for treating or preventing an infection in a subject by use of the polypeptides of the invention, as well as the isolated polynucleotides encoding the polypeptides.

The invention yet further provides a method for modulating an immune response in a subject by use of an agonist or an antagonist of the polypeptides of the invention.

The invention provides a method of treating diseases, such as inflammatory diseases, autoimmune diseases, ischemia related disorders, such as stroke, myocardial infarction, and fulminant liver failure, cancer, and infectious diseases.

The invention identifies nucleotide and polypeptide targets for diagnosis and therapeutic intervention of the disease states described herein, and provides methods for diagnosis and treating these diseases by intervening with these targets. The invention provides the nucleic acid and amino acid sequences of these targets in the Sequence Listing.

The invention provides a first isolated nucleic acid molecule comprising a first polynucleotide or amino acid sequence chosen from chosen from the Sequence Listing; biologically active fragments thereof, and a complement thereof. This first isolated nucleic acid molecule can be chosen from a cDNA molecule, a genomic DNA molecule, a cRNA molecule, a siRNA molecule, a RNAi molecule, an mRNA molecule, an antisense molecule, and a ribozyme. The invention also provides a double-stranded isolated nucleic acid molecule comprising the first nucleic acid molecule and its complement.

The invention also provides a second isolated nucleic acid molecule comprising a second polynucleotide sequence that hybridizes to a first polynucleotide sequence comprising a nucleotide sequence chosen from the Sequence Listing under high stringency conditions.

The invention further provides an isolated polypeptide comprising an amino acid sequence chosen from chosen from the Sequence Listing. It provides an isolated polypeptide encoded by a first nucleic acid molecule as described above.

The invention yet further provides vectors and host cells. It provides a vector comprising a first nucleic acid molecule as described above and a promoter that regulates the expression of the nucleic acid molecule. This promoter can be chosen from one that is naturally contiguous to the nucleic acid molecule and one that is not naturally contiguous to the nucleic acid molecule. It can be an inducible promoter, a conditionally-active promoter (such as the cre-lox promoter), a constitutive promoter, and/or a tissue-specific promoter. Host cells of the invention include recombinant host cells comprising a first nucleic acid molecule as described above, an isolated polypeptide as described above, and the vectors as described above. Host cells of the invention can be prokaryotic cells or eukaryotic cells. Eukaryotic host cells of the invention include human cells, non-human mammalian cells, insect cells, fish cells, plant cells, and fungal cells.

The invention provides a non-human animal injected with the first nucleic acid molecule described above. The animal may be genetically modified with this first nucleic acid molecule. It may be injected with a polypeptide of the invention, as described above.

In another aspect, the invention provides a nucleic acid composition comprising the first nucleic acid molecule described above and a carrier. This carrier may be a pharmaceutically acceptable carrier or an excipient, which may, in turn, be chosen from saline, phosphate buffered saline, and a lipid based formulation. It provides a polypeptide composition comprising a polypeptide as described above and a carrier, which may also be a pharmaceutically acceptable carrier or an excipient. It also provides a vector composition comprising the vector as described above and a carrier; the carrier may also be a pharmaceutically acceptable carrier or an excipient. It further provides a host cell composition comprising the host cell as described above and a carrier; the carrier may also be a pharmaceutically acceptable carrier or an excipient.

In yet another aspect, the invention provides a method of producing a recombinant host cell by providing a composition comprising a vector that comprises the first nucleic acid molecule as described above and allowing a host cell to come into contact with the vector to form a recombinant host cell. The invention provides a method of producing a polypeptide by providing a composition comprising a recombinant host cell as described above and culturing the recombinant host cell to produce the polypeptide. It also provides a method of producing a polypeptide by providing the first nucleic acid as described above and expressing the nucleic acid molecule in a cell free expression system to produce the polypeptide. The cell free expression system can be chosen from a wheat germ lysate expression system, a rabbit reticulocyte expression system, and an *E. coli* lysate expression system.

In yet a further aspect the invention provides a diagnostic kit comprising a composition comprising a first polynucleotide molecule as described above and a vehicle. It also provides a diagnostic kit comprising an antibody that specifically binds to a polypeptide of the invention as described above or a biologically active fragment thereof. It further provides a diagnostic kit comprising a polypeptide of the invention as described above or a biologically active fragment thereof.

The invention provides a method of determining presence of a first polynucleotide molecule as described above by providing this nucleic acid molecule, allowing it to interact with the sample; and determining whether specific binding has occurred. It provides a method of determining the presence of an antibody specific to a polypeptide of the invention as described above or a biologically active fragment thereof by providing a composition comprising the polypeptide, allowing the polypeptide to interact with the sample, and determining whether specific binding has occurred between the polypeptide and the antibody.

The invention provides an antibody that specifically binds to or interferes with activity of a polypeptide of the invention as described above or a biologically active fragment thereof. This antibody may be a polyclonal antibody, a monoclonal antibody, a single chain antibody, and an active fragment of any of these. This antibody may be a fragment, including an antigen binding fragment, an Fc fragment, a cdr fragment, a framework fragment, a variable region of an immunoglobulin, a constant region of an immunoglobulin, and/or a combination thereof. The invention also provides an aptamer that specifically binds to or interferes with the activity of a polypeptide of the invention as described above or a biologically active fragment thereof.

The invention provides a method of treatment of a B-cell deficiency in a subject by providing a composition containing a polypeptide chosen from chosen from the Sequence Listing, or an active fragment thereof, and a carrier; and administering the composition to a subject. This composition may further comprise a soluble factor. Suitable soluble factors for use in the invention include interleukins, for example, IL-7 and cytokines. This method can be used to treat Bruton agammaglobulinemia. It can be performed by administering the composition to a subject either locally or systemically. The carrier may be a pharmaceutically acceptable carrier or an excipient.

The invention also provides a method of treatment of a platelet deficiency in a subject by providing a composition containing a polypeptide chosen from chosen from the Sequence Listing, or an active fragment thereof, and a carrier; and administering the composition to a subject. This method can be used to treat thrombocytopenia. It can be performed by administering the composition to a subject either locally or systemically. The carrier may be a pharmaceutically acceptable carrier or an excipient.

The invention further provides a method of stimulating lymphocyte growth or proliferation in a subject by providing a composition containing the polypeptide chosen from chosen from the Sequence Listing, or an active fragment thereof, and a carrier; and administering the composition to a subject. It can be performed by administering the composition to a subject either locally or systemically. The carrier may be a pharmaceutically acceptable carrier or an excipient. It can be performed by administering the composition after stem cell transplant.

The invention yet further provides a method for treating an adverse effect of a cancer therapy in a subject by administering a composition containing the polypeptide chosen from chosen from the Sequence Listing, or an active fragment thereof, and a carrier, collecting a population of stem cells from the subject, and administering the population of stem cells to the subject. The cancer therapy may be body irradiation, a bone-marrow depleting agent, for example a cytotoxic bone-marrow depleting agent. The method may be performed by administering the stem cells prior to, substantially contemporaneously with, or after the cancer therapy.

The invention provides a method of treating diabetes in a subject by providing a composition containing the polypeptide chosen from chosen from the Sequence Listing, or an active fragment thereof, and a carrier and administering the composition to the subject. It can be performed by administering the composition to a subject either locally or systemically. The carrier may be a pharmaceutically acceptable carrier or an excipient.

The invention also provides a method of promoting angiogenesis in a subject by providing a composition containing the polypeptide chosen from chosen from the Sequence Listing or an active fragment thereof, and a carrier; and the polypeptide chosen from chosen from the Sequence Listing, or an active fragment thereof, and a carrier and administering the composition to the subject. It can be performed by administering the composition to a subject either locally or systemically. The carrier may be a pharmaceutically acceptable carrier or an excipient.

The invention further provides a method of modulating an immune response in a subject by providing a modulator of a polypeptide chosen from any of SEQ. ID. NOS.:9 and 14-16; or an active fragment thereof, and administering the composition to the subject. The modulator may be an antibody, which may, for example, be a monoclonal antibody, a polyclonal antibody, a cdr fragment, a framework fragment, a single chain antibody, and an active fragment of an antibody. This method can be performed to modulate the suppression of inflammation and/or autoimmune diseases. This method can be performed to modulate the immune response by treating rheumatoid arthritis, osteoarthritis, psoriasis, inflammatory bowel disease, multiple sclerosis, systemic lupus erythematosus (SLE), Graves' disease, immunoproliferative disease lymphadenopathy (IPL), angioimmunoproliferative lymphadenopathy (AIL), and/or immunoblastive lymphadenopathy (IBL). This modulation can be performed by administering the composition to the subject locally or systemically in a pharmaceutically acceptable carrier or an excipient.

The invention yet further provides a method for treating or preventing an infection in a subject by providing a composition containing the polypeptide chosen from SEQ. ID. NOS.: 5-6, 19, 26-27, or an active fragment thereof, and a carrier; and administering the composition to a subject. This method can be used to treat or prevent a bacterial infection, a mycoplasma infection, a fungal infection, and/or a viral infection, for example, human immunodeficiency virus (HIV). It can be performed by administering the composition to a subject either locally or systemically. The carrier may be a pharmaceutically acceptable carrier or an excipient.

The invention provides a method for treating or preventing an ischemic disease, including but not limited to stroke, myocardial infarction, and fulminant liver failure, in a subject by providing a composition containing a polynucleotide or polypeptide chosen from the Sequence Listing or an active fragment thereof, and a carrier. It can be performed by administering the composition to a subject either locally or systemically. The carrier may be a pharmaceutically acceptable carrier or an excipient.

The invention also provides a method for inhibiting tumor growth in a subject by providing a composition containing a polynucleotide or polypeptide chosen from the Sequence Listing or an active fragment thereof, and a carrier. It can be performed by administering the composition to a subject either locally or systemically. The carrier may be a pharmaceutically acceptable carrier or an excipient. This method can be performed to inhibit tumor growth, wherein the tumor is comprised of solid tumor cells or leukemic cells.

The invention further provides a method of treating a cancer in a subject by providing a composition containing a polynucleotide or polypeptide chosen from the Sequence Listing or an active fragment thereof, and a carrier. It can be performed by administering the composition to a subject either locally or systemically. The carrier may be a pharmaceutically acceptable carrier or an excipient. This method can be performed to treat cancer, wherein the cancer is a solid tumor or a leukemia.

The invention yet further provides a method of treating a cancer in a subject by providing a composition containing a polynucleotide or polypeptide chosen from the Sequence Listing or an active fragment thereof, and a carrier. It can be performed by administering the composition to a subject either locally or systemically. The carrier may be a pharmaceutically acceptable carrier or an excipient. This method can be performed to treat an allergy, wherein the allergy is asthma.

In another aspect, the invention provides for the use of the polynucleotides or polypeptides of the Sequence Listing or an active fragment thereof as a target for screening for a modulator. Targets can include a small molecule drug, an antibody, and an aptamer.

The invention provides a method of modulating an immune condition in a subject by providing a modulator of a polypeptide chosen from the Sequence Listing and active fragments thereof; and administering the modulator to the subject. The modulator can be an antibody and the antibody can be a monoclonal antibody, a polyclonal antibody, a cdr fragment, a framework fragment, a single chain antibody, and/or an active fragment of an antibody. The immune condition may comprise inflammation and the modulation may comprise suppression. The immune condition may comprise autoimmune disease and the modulation may comprise suppression. The immune condition may comprise rheumatoid arthritis, osteoarthritis, psoriasis, inflammatory bowel disease, multiple sclerosis, myocardial infarction, stroke, and/or fulminant liver failure. The modulation may comprise suppression.

The invention also provides a method of enhancing immune response to a vaccine in a subject by providing a polypeptide composition comprising a substantially purified polypeptide chosen from the Sequence Listing and active fragments thereof; providing a vaccine composition; and administering the polypeptide composition and the vaccine composition to the subject. The polypeptide composition may be administered to the subject prior to, substantially contemporaneously with, or after administering the vaccine composition.

The invention provides a method for promoting tissue regeneration in a subject by providing a nucleic acid molecule comprising a polynucleotide or polypeptide sequence chosen from chosen from the Sequence Listing; a polynucleotide sequence encoding a nucleotide chosen from chosen from the Sequence Listing; biologically active fragments of these, and/or complements of these and administering the nucleic acid to the subject. The method can be performed by administering the molecule locally, for example, into a tissue. Suitable tissues include brain, heart, pancreas, lung, liver, and bone. The method can be performed wherein the molecule is present in a cell, for example, a heart cell, a brain cell, a pancreatic cell, a lung cell, a liver cell, or a bone cell. The heart cell may, for example, be a cardiac fibroblast.

The invention also provides a method for promoting tissue regeneration in a subject by providing a polypeptide comprising an amino acid sequence chosen from chosen from the Sequence Listing; biologically active fragments of these, and complements of these; and administering the amino acid sequence to the subject. The method can be performed by administering the molecule locally, for example, into a tissue. Suitable tissues include brain, heart, pancreas, lung, liver and bone. The method can be performed wherein the molecule is present in a cell, for example, a heart cell, a brain cell, a pancreatic cell, a lung cell, a liver cell, or a bone cell. This method can be performed by administering one or more stem cells to the subject prior to, substantially contemporaneously with, or after administering the nucleic acid molecule or polypeptide. In an embodiment, the method is performed by transfecting the cells of a subject with SDF-1, providing them to an organ of the subject, and providing the subject with stem cells, for example, mesenchymal stem cells, either before, during, or after providing the transfected cells. In an embodiment, the method is performed by transfecting the cardiac cells of a subject with SDF-1, providing them to the heart, for example by injection, and providing the subject with stem cells, for example, mesenchymal stem cells, either before, during, or after the transfected cardiac cells.

The invention provides a cell transfected with an isolated nucleic acid molecule comprising a first polynucleotide sequence chosen from SEQ. ID. NOS.:1, 6-8, and 17; a polynucleotide sequence encoding a polypeptide of SEQ. ID. NO.:9, 14-16, 22-23; biologically active fragments thereof, and a complement thereof. This cell may be a heart cell, a brain cell, a pancreatic cell, a lung cell, a liver cell, a skin cell, a bone cell, a mesenchymal stem cell, a progenitor cell, an adult stem cell, or an embryonic stem cell.

The invention provides a method of treating a subject who can benefit from receiving such a polynucleotide, or an isolated polypeptide comprising an amino acid sequence, wherein the amino acid sequence is chosen from SEQ. ID. NO.:9, 14-16, and 22-23 by providing a composition comprising such a polynucleotide or polypeptide and administering the composition to the subject. The subject may be treated for a cardiovascular disease, brain disease, cancer, infection, diabetes, bone disease, lung disease, liver disease, skin disease, burn, stroke, trauma, injury, or deficiency. The composition may further comprise a pharmaceutically acceptable carrier or excipient. It may be administered locally or systemically. The composition may be administered in combination with another therapeutic, wherein the other therapeutic, for example, a growth factor or cytokine, is administered before, after, or substantially contemporaneously with the composition. The composition is administered at a therapeutically effective dose.

Suitable growth factors include fibroblast growth factor, platelet derived growth factor, insulin-like growth factor, epidermal growth factor, GCSF, GM-CSF, TGF-α, TGF-β, PD-ECGF, pre-B cell enhancing factor (PBEF), an osteogenic factor, c-kit ligand, stem cell factor, TNF-α, and muteins or variants of any of these which have growth factor activity. The fibroblast growth factor may be chosen from FGF2, FGF4, FGF8, FGF9, and muteins or variants of any of these which have growth factor activity. Suitable platelet derived growth factors include PDGF-AA, PDGF-BB, PDGF-AB, and muteins or variants of any of these which have growth factor activity. Suitable cytokines include IL-13.

The invention provides a polypeptide comprising the amino acid sequence of amino acids 22-88 of CLN00235738_5pv1.a and further comprising at least one additional amino acid chosen from amino acids 89-140, wherein polypeptide comprises a contiguous sequence of amino acids chosen from CLN00235738_5pv1.a as shown in FIG. 1.

DEFINITIONS

The terms used herein have their ordinary meanings, as set forth below, and can be further understood in the context of the specification.

The terms "polynucleotide," "nucleotide," "nucleic acid," "nucleic acid molecule," "nucleic acid sequence," "polynucleotide sequence," and "nucleotide sequence" are used interchangeably herein to refer to polymeric forms, both double- and single-stranded, of nucleotides of any length. The polynucleotides can contain deoxyribonucleotides, ribonucleotides, and/or their analogs or derivatives.

The terms "polypeptide," "peptide," and "protein," used interchangeably herein, refer to a polymeric form of amino acids of any length, which can include naturally-occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. The term includes single chain protein as well as multimers. The term also includes conjugated proteins, fusion proteins, including, but not limited to, glutathione S-transferase (GST) fusion proteins, fusion proteins with a heterologous amino acid sequence, fusion proteins with heterologous and homologous leader sequences, fusion proteins with or without N-terminal methionine residues, pegolyated proteins, and immunologically tagged, or his-tagged proteins. The term also includes peptide aptamers.

An "isolated," "purified," "substantially isolated," or "substantially purified" molecule (such as a polypeptide or polynucleotide) is one that has been manipulated to exist in a higher concentration than in nature. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. As used herein, an "isolated," "purified," "substantially isolated," or "substantially purified" molecule includes recombinant molecules.

By "fragment" is intended a polynucleotide or polypeptide consisting of only a part of the intact full-length or naturally occurring polynucleotide or polypeptide sequence and structure. A polypeptide fragment can include e.g., a C-terminal deletion, an N-terminal deletion, and/or an internal deletion of a native polypeptide or an extracellular domain of a transmembrane protein. A fragment of a protein will generally include at least about 5-10, 15-25, or 20-50 or more contiguous amino acid residues of the full-length molecule, at least about 15-25 contiguous amino acid residues of the full-length molecule, or any integer between 5 amino acids and the full-length sequence.

A "complement" of a nucleic acid molecule is a one that is comprised of its complementary base pairs. Deoxyribonucleotides with the base adenine are complementary to those with the base thymidine, and deoxyribonucleotides with the base thymidine are complementary to those with the base adenine. Deoxyribonucleotides with the base cytosine are complementary to those with the base guanine, and deoxyribonucleotides with the base guanine are complementary to those with the base cytosine. Ribonucleotides with the base adenine are complementary to those with the base uracil, and deoxyribonucleotides with the base uracil are complementary to those with the base adenine. Ribonucleotides with the base cytosine are complementary to those with the base guanine, and deoxyribonucleotides with the base guanine are complementary to those with the base cytosine.

A "promoter," as used herein, is a DNA regulatory region capable of binding RNA polymerase in a mammalian cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain "TATA" boxes and "CAT" boxes. Promoters include those that are naturally contiguous to a nucleic acid molecule and those that are not naturally contiguous to a nucleic acid molecule. Additionally, a promoter includes inducible promoters, conditionally active promoters, such as a cre-lox promoter, constitutive promoters, and tissue specific promoters.

A "vector" is a plasmid that can be used to transfer DNA sequences from one organism to another or to express a gene of interest.

"Expression of a nucleic acid molecule" refers to the conversion of the information contained in the molecule, into a gene product. A gene product can be the direct transcriptional product of a gene (e.g., mRNA, tRNA, rRNA, antisense RNA, ribozyme, structural RNA, or any other type of RNA) or a peptide or polypeptide produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

The term "host cell" includes an individual cell, cell line, cell culture, or cell in vivo, which can be or has been a recipient of any polynucleotides or polypeptides of the invention, for example, a recombinant vector, an isolated polynucleotide, an antibody or a fusion protein. Host cells include progeny of a single host cell, and the progeny may not necessarily be completely identical (in morphology, physiology, or in total DNA, RNA, or polypeptide complement) to the original parent cell due to natural, accidental, or deliberate mutation and/or change. Host cells can be prokaryotic or eukaryotic, including mammalian, insect, amphibian, reptilian, crustacean, avian, fish, plant, and fungal cells. A host cell includes cells transformed, transfected, transduced, or infected in vivo or in vitro with a polynucleotide of the invention, for example, a recombinant vector. A host cell which comprises a recombinant vector of the invention may be called a "recombinant host cell."

The term "recombinant" as used with respect to a host cell means a host cell into which a recombinant polynucleotide has been introduced.

A "biologically active" entity, or an entity having "biological activity," is one or more entity having structural, regulatory, or biochemical functions of a naturally occurring molecule or any function related to or associated with a metabolic or physiological process. Biologically active polynucleotide fragments are those exhibiting activity similar, but not necessarily identical, to an activity of a polynucleotide of the present invention. The biological activity can include an improved desired activity, or a decreased undesirable activity. For example, an entity demonstrates biological activity when it participates in a molecular interaction with another molecule, such as hybridization, when it has therapeutic value in alleviating a disease condition, when it has prophylactic value in inducing an immune response, when it has diagnostic value in determining the presence of a molecule, such as a biologically active fragment of a polynucleotide that can, for example, be detected as unique for the polynucleotide molecule, or that can be used as a primer in a polymerase chain reaction. A biologically active polypeptide or fragment thereof includes one that can participate in a biological reaction, for example, one that can serve as an epitope or immunogen to stimulate an immune response, such as production of antibodies, or that can participate in stimulating or inhibiting signal transduction by binding to ligands receptors or other proteins, or nucleic acids; or activating enzymes or substrates.

The terms "antibody" and "immunoglobulin" refer to a protein, for example, one generated by the immune system, synthetically, or recombinantly, that is capable of recognizing and binding to a specific antigen; antibodies are commonly known in the art. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, $F(ab')_2$ and $F(ab)$ fragments; Fv molecules (for example, noncovalent heterodimers), dimeric and trimeric antibody fragment constructs; minibodies, humanized antibody molecules, and any functional fragments obtained from such molecules, wherein such fragments retain specific binding.

The term "specific binding," in the context of antibody binding, refers to high avidity and/or high affinity binding of an antibody to a specific epitope. Hence, an antibody that binds specifically to one epitope (a "first epitope") and not to another (a "second epitope") is a "specific antibody." An antibody specific to a first epitope may cross react with and bind to a second epitope if the two epitopes share homology or other similarity.

The term "specific binding," in the context of a polynucleotide, refers to hybridization under stringent conditions. Conditions that increase stringency of both DNA/DNA and DNA/RNA hybridization reactions are widely known and published in the art. See, for example, Sambrook, Sambrook et al. *Molecular Cloning, A Laboratory Manual,* 2000.

"Subject," "individual," "host," and "patient" are used interchangeably herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

A "patient sample" is any biological specimen derived from a patient; the term includes, but is not limited to, biological fluids such as blood, serum, plasma, urine, cerebrospinal fluid, tears, saliva, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization, or enrichment for certain components, such as polynucleotides or polypeptides. Also included in the term are derivatives and fractions of patient samples. A patient sample may be used in a diagnostic, prognostic, or other monitoring assay.

The term "modulate" refers to the production, either directly or indirectly, of an increase or a decrease, a stimulation, inhibition, interference, or blockage in a measured activity when compared to a suitable control. A "modulator" of a polypeptide or polynucleotide or an "agent" are terms used interchangeably herein to refer to a substance that affects, for example, increases, decreases, stimulates, inhibits, interferes with, or blocks a measured activity of the polypeptide or polynucleotide, when compared to a suitable control. An agent which modulates a biological activity of a subject polypeptide or polynucleotide increases or decreases the activity or binding at least about 10%, at least about 15%, at least about 20%, at least about 25%, at least about 50%, at least about 80%, or at least about 2-fold, at least about 5-fold, or at least about 10-fold or more when compared to a suitable control.

"Treatment," as used herein, covers any administration or application of remedies for disease in a mammal, including a human, and includes inhibiting the disease, i.e., arresting its development, or relieving the disease, i.e., causing regression, or restoring or repairing a lost, missing, or defective function; or stimulating an inefficient process. In the context of cancer, the term "treating" includes any or all of: preventing growth of tumor cells or cancer cells, preventing replication of tumor cells or cancer cells, lessening of overall tumor burden and ameliorating one or more symptoms associated with the disease. In the context of an autoimmune disease, the term "treating" includes any or all of: preventing replication of cells associated with an autoimmune disease state including, but not limited to, cells capable of producing an autoimmune antibody, lessening the autoimmune-antibody burden and ameliorating one or more symptoms of an autoimmune disease. In the context of an infectious disease, the term "treating" includes any or all of preventing the growth, multiplication or replication of the pathogen that causes the infectious disease and ameliorating one or more symptoms of an infectious disease. In the context of an ischemic disease, the term "treating" includes any or all of preventing the growth, multiplication or replication of the pathogen that causes the ischemic disease and ameliorating one or more symptoms of an ischemic disease.

"Preventing," as used herein, includes providing prophylaxis with respect to the occurrence or recurrence of a disease in a subject that may be predisposed to the disease but has not yet been diagnosed with the disease. Treatment and prophylaxis can be administered to an organism, including a human, or to a cell in vivo, in vitro, or ex vivo, and the cell subsequently administered to the subject.

"Disease" refers to any condition, infection, disorder, or syndrome that requires medical intervention or for which medical intervention is desirable. Such medical intervention can include treatment, diagnosis, and/or prevention.

"Cancer" is any abnormal cell or tissue growth, for example, a tumor, whether malignant, pre-malignant, or non-malignant. It is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type.

A "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

A "composition" herein refers to a composition that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses, or powders.

Nucleic Acids and Polypeptides

The present invention provides nucleic acid molecules containing a polynucleotide encoding a newly identified SDF-1 variant polypeptide having the amino acid sequences as shown in the Sequence Listing (SEQ. ID. NO.:9). The isolated SDF-1 variants of the invention were identified by bioinformatic analysis of multiple SDF-1 clones.

Fragments of the full length SDF-1 and SDF-1 variants may be used as hybridization probes for cDNA libraries to isolate the full length gene and to isolate other genes which have a high sequence similarity or a similar biological activity. Probes of this type can have at least 30 bases and may comprise, for example, 50 or more bases. The probe may also be used in a screening procedure to identify a cDNA clone corresponding to a full length transcript and a genomic clone or clones that contain complete SDF-1 genes, including regulatory and promoter regions, exons, and introns. An example of such a screen would include isolating the coding regions of SDF-1 genes by using a known nucleic acid sequence to synthesize an oligonucleotide probe. Labeled oligonucleotides having a sequence complementary to a gene of the present invention can be used to screen a human cDNA, a genomic DNA, or a mRNA library to identify complementary library components.

The present invention further relates to polynucleotides which hybridize to the described sequences if there is at least 91%, at least 92%, or at least 95% identity between the sequences. The present invention relates to polynucleotides which hybridize under stringent conditions to the described polynucleotides. Stringent conditions generally include condition under which hybridization will occur only if there is at least 95%, or at least 97% identity between the sequences. For example, overnight incubation at 42° C. in a solution containing 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C., constitute stringent conditions. The polynucleotides which hybridize to the hereinabove described polynucleotides encode polypeptides which may retain substantially the same biological function or activity as the mature polypeptide.

Alternatively, the polynucleotide may have at least 20 bases, at least 30 bases, or at least 50 bases which hybridize to a polynucleotide of the present invention and which has an identity thereto, as hereinabove described, and which may or may not retain activity.

Thus, the present invention is directed to polynucleotides having at least a 70% identity, at least a 90% identity, or at least a 95% identity to a polynucleotide which encodes the polypeptides set forth in the Sequence Listing, as well as fragments thereof, which fragments have at least 30 bases or at least 50 bases, and to polypeptides encoded by such polynucleotides.

Using the information provided herein, such as the nucleotide sequences set forth in the Sequence Listing, nucleic acid molecules of the present invention encoding a SDF-1 polypeptide may be obtained using standard cloning and screening procedures, such as those for cloning cDNAs using mRNA as starting material. Nucleic acids of the invention are useful as hybridization probes for differential identification of the tissue(s) or cell type(s) present in a biological sample. Polypeptides and antibodies directed to those polypeptides are useful for providing immunological probes for the differential identification of tissues or cell types.

Polypeptides and Fragments

The invention further provides an isolated SDF-1 and SDF-1 polypeptide containing the amino acid sequences encoded by the nucleotide sequences set forth in the Sequence Listing, the amino acid sequences set forth in the Sequence Listing, or a peptide or polypeptide comprising a fragment of such a polypeptide.

Variant and Mutant Polynucleotides

The present invention further relates to variants of the nucleic acid molecules of the present invention, which encode portions, analogs, or derivatives of the SDF-1 molecules. Variants may occur naturally, such as a natural allelic variant, i.e., one of several alternate forms of a gene occupying a given chromosomal locus *Genes II*, Lewin, B., ed., John Wiley & Sons, New York (1985)). Non-naturally occurring variants may be produced using art-known mutagenesis techniques.

Such variants include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions. These may take the form of silent substitutions, additions, or deletions which do not alter the properties or activities of the described SDF-1 proteins, or portions thereof.

In an embodiment, the invention provides nucleic acid molecules encoding mature proteins, i.e., those with cleaved signal peptide or leader sequences, e.g., as shown in the Sequence Listing. Further embodiments include an isolated nucleic acid molecule comprising a polynucleotide having a nucleotide sequence at least 93% identical, or at least 95%, 96%, 97%, 98%, or 99% identical to a polynucleotide from the Sequence Listing, a polypeptide encoded by a polynucleotide shown in the Sequence Listing, a polypeptide shown in the Sequence Listing, or a biologically active fragment of any of these.

A polynucleotide having a nucleotide sequence at least, for example, 95% identical to a reference nucleotide sequence encoding an SDF-1 polypeptide is one in which the nucleotide sequence is identical to the reference sequence except that it may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 93%, 95%, 96%, 97%, 98%, or 99% identical to, for instance, the nucleotide sequences set forth in the Sequence Listing can be determined conventionally using known computer programs such as the Bestfit program (Wisconsin Sequence Analysis Package, Version 8 for Unix, Genetics Computer Group, Madison, Wis.). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 93%, 95%, 96%, 97%, 98%, or 99% identical to the nucleic acid sequences set forth in the Sequence Listing irrespective of whether they encode a polypeptide having SDF-1 activity. Even where a particular nucleic acid molecule does not encode a polypeptide having SDF-1 activity, one of skill in the art would know how to use the nucleic acid molecule, for instance, as a hybridization probe or a polymerase chain reaction (PCR) primer. Uses of the nucleic acid molecules of the present invention that do not encode a polypeptide having SDF-1 activity include, inter alia, (1) isolating the SDF-1 gene or allelic variants thereof in a cDNA library; (2) in situ hybridization (e.g., "FISH") to metaphase chromosomal spreads to provide the precise chromosomal location of the SDF-1 genes, as described in Verna et al., *Human Chromosomes: A Manual of Basic Techniques*, Pergamon Press, New York (1988); and Northern blot analysis for detecting SDF-1 mRNA expression in specific tissues.

The present application is also directed to nucleic acid molecules having sequences at least 93%, 95%, 96%, 97%, 98%, or 99% identical to a nucleic acid sequence of the Sequence Listing which, encode a polypeptide having SDF-1 polypeptide activity, i.e., a polypeptide exhibiting activity either identical to or similar, but not identical, to an activity of the SDF-1 polypeptides of the invention, as measured in a particular biological assay. For example, the SDF-1 polypeptides of the present invention may either stimulate or inhibit the proliferation of various mammalian cells, as demonstrated below.

Of course, due to the degeneracy of the genetic code, one of ordinary skill in the art will immediately recognize that a large number of the nucleic acid molecules having a sequence at least 93%, 95%, 96%, 97%, 98%, or 99% identical to the nucleic acid sequence of the nucleic acid sequences set forth in the Sequence Listing will encode a polypeptide having SDF-1 polypeptide activity. In fact, since multiple degenerate variants of these nucleotide sequences encode the same polypeptide, this will be clear to the skilled artisan even without performing the above described comparison assay. It will be further recognized in the art that a reasonable number of nucleic acid molecules that are not degenerate variants will also encode a polypeptide having SDF-1 polypeptide activity, the skilled artisan is fully aware of amino acid substitutions that are either less likely or not likely to significantly affect protein function (e.g., replacing one aliphatic amino acid with a second aliphatic amino acid), as further described below.

Vectors and Host Cells

The present invention also relates to vectors which include the isolated nucleic acid molecules of the present invention, host cells which are genetically engineered with the recombinant vectors, and the production of SDF-1 polypeptides or fragments thereof by recombinant techniques. The vector may be, for example, a phage, plasmid, viral, or retroviral vector. Retroviral vectors may be replication competent or replication defective. In the latter case, viral propagation generally will occur only in complementing host cells.

The present invention provides recombinant vectors that contain, for example, nucleic acid constructs that encode secretory leader sequences and a selected heterologous polypeptide of interest, and host cells that are genetically engineered with the recombinant vectors. Selected heterologous polypeptides of interest in the present invention include, for example, an extracellular fragment of a secreted protein, a type I membrane protein, a type II membrane protein, a multi-membrane protein, and a soluble receptor. These vectors and host cells can be used for the production of polypeptides described herein, including fragments thereof by conventional recombinant techniques. The vector may be, for example, a phage, plasmid, viral or retroviral vector. Retroviral vectors may be replication competent or replication defective. As above, in the latter case, viral propagation generally will occur only in complementing host cells.

The polynucleotides may be joined to a vector containing a secretory leader sequence and a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert can be operatively linked to an appropriate promoter, such as the phage lambda PL promoter; the E. coli lac, trp, phoA and tac promoters; the SV40 early and late promoters; and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs can include a translation initiating codon at the beginning and a termination codon (UAA, UGA, or UAG) appropriately positioned at the end of the polypeptide to be translated.

As indicated, the expression vectors may include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

The selectable markers are genes that confer a phenotype on a cell expressing the marker, so that the cell can be identified under appropriate conditions. Generally, a selectable marker allows the selection of transformed cells based on their ability to thrive in the presence or absence of a chemical or other agent that inhibits an essential cell function. Suitable markers, therefore, include genes coding for proteins which confer drug resistance or sensitivity thereto, impart color to, or change the antigenic characteristics of those cells transfected with a molecule encoding the selectable marker, when the cells are grown in an appropriate selective medium. For example, selectable markers include cytotoxic markers and drug resistance markers, whereby cells are selected by their ability to grow on media containing one or more of the cytotoxins or drugs; auxotrophic markers by which cells are selected for their ability to grow on defined media with or without particular nutrients or supplements, such as thymidine and hypoxanthine; metabolic markers for which cells are selected, e.g., their ability to grow on defined media containing the appropriate sugar as the sole carbon source, and markers which confer the ability of cells to form colored colonies on chromogenic substrates or cause cells to fluoresce.

Among vectors suitable for use in bacteria include pQE70, pQE60, and pQE-9, available from QIAGEN, Inc., (Mississauga, Ontario, Canada); pBS vectors, Phagescript vectors, Bluescript vectors, pNH8A, pNH6a, pNH18A, pNH46A, available from Stratagene (La Jolla, Calif.); and ptrc99a, pKK223-3, pKK233-3, pDR540, pRIT5 available from Pharmacia (Peapack, N.J.). Among suitable eukaryotic vectors are pWLNEO, pSV2CAT, pOG44, pXT1, and pSG available from Stratagene; and pSVK3, pBPV, pMSG and pSVL, available from Pharmacia. Other suitable vectors will be readily apparent to the skilled artisan.

Other suitable vectors include those employing a pTT vector backbone (Durocher et al. Nucl. Acids Res. 30 (2002)). Briefly, the p'1"1' vector backbone may be prepared by obtaining pIRESpuro/EGFP (pEGFP) and pSEAP basic vector(s), for example from Clontech (Palo Alto, Calif.), and pcDNA3.1, pcDNA3.1/Myc-(His)$_6$ and pCEP4 vectors can be obtained from, for example, Invitrogen. SuperGlo GFP variant (sgGFP) can be obtained from Q-Biogene (Carlsbad, Calif.). Preparing a pCEP5 vector can be accomplished by removing the CMV promoter and polyadenylation signal of pCEP4 by sequential digestion and self-ligation using SalI and XbaI enzymes resulting in plasmid pCEP4Δ. A GblII fragment from pAdCMV5 (Massie et al., J. Virol., 72: 2289-2296 (1998)), encoding the CMV5-poly(A) expression cassette may be ligated in BglII-linearized pCEP4Δ, resulting in pCEP5 vector. The pTT vector can be prepared by deleting the hygromycin (BsmI and SalI excision followed by fill-in and ligation) and EBNA1 (ClaI and NsiI excision followed by fill-in and ligation) expression cassettes. The ColEI origin (FspI-SalI fragment, including the 3' end of β-lactamase ORF) can be replaced with a FspI-SalI fragment from pcDNA3.1 containing the pMBI origin (and the same 3' end of β-lactamase ORF). A Myc-(His)$_6$ C-terminal fusion tag can be added to SEAP (HindIII-HpaI fragment from pSEAP-basic) following in-frame ligation in pcDNA3.1/Myc-His digested with HindIII and EcoRV. Plasmids can subsequently be amplified in E. coli (DH5α) grown in LB medium and purified using MAXI prep columns (Qiagen, Mississauga, Ontario, Canada). To quantify, plasmids can be subsequently diluted in 50 mM Tris-HCl pH 7.4 and absorbencies can be measured at 260 nm and 280 nm. Plasmid preparations with $A_{260}/A_{280}$ ratios between about 1.75 and about 2.00 are suitable.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., *Basic Methods In Molecular Biology* (1986).

The polypeptides may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide.

The addition of peptide moieties to polypeptides to engender secretion or excretion, to improve stability and to facilitate purification, among others, are familiar and routine techniques in the art. A suitable fusion protein may comprise a heterologous region from immunoglobulin that is useful to stabilize and purify proteins. For example, EP-A-O 464 533 (Canadian counterpart 2045869) discloses fusion proteins containing various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected, and purified in the advantageous manner described. This is the case when the Fc portion proves to be a hindrance to use in therapy and diagnosis, for example when the fusion protein is to be used as an antigen for immunizations. In drug discovery, for example, human proteins, such as hIL-5, have been fused with Fc portions for the purpose of high-throughput screening assays to identify antagonists. See, Bennett et al., *J. Molec. Recog.*, 8:52-58 (1995) and Johanson et al, *J. Biol. Chem.*, 270:9459-9471 (1995).

The SDF-1 polypeptides can be recovered and purified from recombinant cell cultures by well-known methods, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography (HPLC) can be employed for purification. Polypeptides of the present invention include products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Typically, a heterologous polypeptide, whether modified or unmodified, may be expressed as described above, or as a fusion protein, and may include not only secretion signals, but also a secretory leader sequence. A secretory leader sequence of the invention directs certain proteins to the endoplasmic reticulum (ER). The ER separates the membrane-bound proteins from other proteins. Once localized to the ER, proteins can be further directed to the Golgi apparatus for distribution to vesicles; including secretory vesicles; the plasma membrane, lysosomes, and other organelles.

Proteins targeted to the ER by a secretory leader sequence can be released into the extracellular space as a secreted protein. For example, vesicles containing secreted proteins can fuse with the cell membrane and release their contents into the extracellular space—a process called exocytosis. Exocytosis can occur constitutively or after receipt of a triggering signal. In the latter case, the proteins may be stored in secretory vesicles (or secretory granules) until exocytosis is triggered. Similarly, proteins residing on the cell membrane can also be secreted into the extracellular space by proteolytic cleavage of a "linker" holding the protein to the membrane.

Additionally, peptide moieties and/or purification tags may be added to the polypeptide to facilitate purification. Such regions may be removed prior to final preparation of the polypeptide. The addition of peptide moieties to polypeptides to engender secretion or excretion, to improve stability, and to facilitate purification, among other reasons, are familiar and routine techniques in the art. Suitable purification tags include, for example, V5, HISX6, HISX8, avidin, and biotin.

The invention provides a fusion protein comprising a heterologous region from an immunoglobulin that is useful to stabilize and purify proteins. For example, EP-A-O 464 533 (Canadian counterpart 2045869) discloses fusion proteins containing various portions of constant region of immunoglobulin molecules together with another human protein or part thereof. In many cases, the Fc part of a fusion protein is advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected, and purified in the advantageous manner described. This is the case when the Fc portion proves to be a hindrance to use in therapy and/or diagnosis, for example, when the fusion protein is to be used as an antigen for immunizations. In drug discovery, for example, human proteins, such as hIL-5, have been fused with Fc portions for the purpose of high-throughput screening assays to identify antagonists of hIL-5. See, Bennett et al., *J. Molec. Recog.*, 8:52-58 (1995) and Johanson et al, *J. Biol. Chem.*, 270:9459-9471 (1995).

A heterologous polypeptide of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, and high performance liquid chromatography (HPLC). Polypeptides of the present invention include products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells, or from a cell free expression system. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

Polypeptides and Fragments

The invention further provides isolated SDF-1 polypeptides containing the amino acid sequences encoded by the nucleotide sequences set forth in the Sequence Listing, the amino acid sequences set forth in the Sequence Listing, and polypeptides comprising a fragment of any of these.

The invention provides secreted proteins, which are capable of being directed to the endoplasmic reticulum (ER), secretory vesicles, or the extracellular space as a result of a secretory leader, signal peptide, or leader sequence, as well as proteins released into the extracellular space without necessarily containing a signal sequence. If a secreted protein is released into the extracellular space, it may undergo extracellular processing to a mature polypeptide. Release into the extracellular space can occur by many mechanisms, including exocytosis and proteolytic cleavage.

The sequences of the invention encompass a variety of different types of nucleic acids and polypeptides with different structures and functions. They can encode or comprise polypeptides belonging to different protein families (Pfam). The "Pfam" system is an organization of protein sequence classification and analysis, based on conserved protein domains; it can be publicly accessed in a number of ways, for example, at http://pfam.wustl.edu. Protein domains are portions of proteins that have a tertiary structure and sometimes have enzymatic or binding activities; multiple domains can be connected by flexible polypeptide regions within a protein. Pfam domains can comprise the N-terminus or the C-terminus of a protein, or can be situated at any point in between. The Pfam system identifies protein families based on these domains and provides an annotated, searchable database that classifies proteins into families (Bateman et at, *Nucl. Acids Res.* 30:276-280 (2002)). Sequences of the invention can encode or be comprised of more than one Pfam.

Sequences of the invention may comprise an IL8 Pfam domain, as further described below. Interleukin 8 (IL-8) is a chemokine that has been reported, inter alia, to play a role in metastatic human cancer (Xie, *Cytokine Growth Factor Rev.* 12(4):375-391 (2001)) and in the airway epithelium (Strieter, *Am. J. Physiol. Lung Cell Mol. Physiol.* 283(4):L688-689 (2002). The IL8 Pfam includes a number of IL-8-like secreted growth factors and interferons involved in mitogenic, chemotactic, and inflammatory activity. Members of the Pfam are generally characterized by a structure containing two conserved disulfide bonds (http://pfam.wustl.edu/cgi-bin/getdesc?name=IL8).

Variant and Mutant Polypeptides

Protein engineering may be employed to improve or alter the characteristics of SDF-1 polypeptides of the invention. Recombinant DNA technology known to those skilled in the art can be used to create novel mutant proteins or "muteins" including single or multiple amino acid substitutions, deletions, additions, or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984-2988 (1993), reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or mature from of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. Accordingly, the present invention further provides polypeptides having one or more residues deleted from the amino terminus of the amino acid sequences of the SDF-1 molecules as shown in the Sequence Listing.

Similarly, many examples of biologically functional C-terminal deletion muteins are known. For instance, interferon gamma increases in activity as much as ten fold when 8-10 amino acid residues are deleted from the carboxy terminus of the protein, see, for example, Dobeli et al., *J. Biotechnology*, 7:199-216 (1988).

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Other Mutants

In addition to terminal deletion forms of the protein discussed above, it also will be recognized by one of ordinary skill in the art that some amino acid sequences of the SDF-1 polypeptides can be varied without significant effect of the structure or function of the protein. If such differences in sequence are contemplated, it should be remembered that there will be critical areas on the protein which determine activity.

Thus, the invention further includes variations of the SDF-1 polypeptides which show substantial SDF-1 polypeptide activity or which include regions of the SDF-1 proteins such as the protein portions discussed below. Such mutants include deletions, insertions, inversions, repeats, and type substitutions, selected according to general rules known in the art, so as have little effect on activity. For example, guidance concerning how to make phenotypically silent amino acid substitutions is provided in Bowie et al., *Science*, 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections, or screens, to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, et al., supra, and the references cited therein. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, and replacements between the aromatic residues Phe and Tyr.

Thus, a fragment, derivative, or analog of a polypeptide of the Sequence Listing or polypeptide encoded by a nucleic acid sequence of the Sequence Listing may be (i) one in which one or more of the amino acid residues are substituted with a conserved or non-conserved amino acid residue; such a substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the above form of the polypeptide, such as an IgG Fc fusion region peptide, a leader or secretory sequence, a sequence employed to purify the above form of the polypeptide, or a proprotein sequence. Such fragments, derivatives, and analogs are deemed to be within the scope of those skilled in the art from the teachings herein.

Thus, the SDF-1 polypeptides of the present invention may include one or more amino acid substitutions, deletions, or additions, either from natural mutations or human manipulation. As indicated, these changes may be of a minor nature, such as conservative amino acid substitutions, that do not significantly affect the folding or activity of the protein. Conservative amino acid substitutions include the aromatic substitutions Phe, Trp, and Tyr; the hydrophobic substitutions Leu, Iso, and Val; the polar substitutions Glu and Asp; the basic substitutions Arg, Lys, and His; the acidic substitutions Asp and Glu; and the small amino acid substations Ala, Ser, Thr, Met, and Gly.

Amino acids essential for the functions of SDF-1 polypeptides can be identified by methods known in the art, such as site-directed mutagenesis or alanine-scanning mutagenesis, see, for example, Cunningham and Wells, *Science,* 244:1081-1085 (1989). The latter procedure introduces single alanine mutations. The resulting mutant molecules are then tested for biological activity such as receptor binding, or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because, for example, aggregates can be immunogenic, Pinckard et al., *Clin. Exp. Immunol.,* 2:331-340 (1967); Robbins et al., *Diabetes,* 36:838-845 (1987); Cleland et al., *Crit. Rev. Therapeutic Drug Carrier Systems,* 10:307-377 (1993).

Replacing amino acids can also change the selectivity of the binding of a ligand to cell surface receptors. For example, Ostade et al., *Nature,* 361:266-268 (1993) describes certain mutations resulting in selective binding of TNF-α to only one of the two known types of TNF receptors. Sites that are critical for ligand-receptor binding can also be determined by structural analysis such as crystallization, nuclear magnetic resonance, or photoaffinity labeling, for example, Smith et al., *J. Mol. Biol.,* 224:899-904 (1992) and de Vos et al., *Science,* 255:306-312 (1992).

The polypeptides of the present invention can be provided in an isolated form, and can be substantially purified. A recombinantly produced version of the herein described SDF-1 polypeptides can be substantially purified, e.g., by the one-step method described in Smith and Johnson, *Gene,* 67:31-40 (1988). Polypeptides of the invention also can be purified from natural or recombinant sources using anti-SDF-1 antibodies of the invention using methods which are well known in the art of protein purification. The polypeptides herein may be purified or isolated in the presence of ions or agents that aid in the refolding of the molecules or aid in dimerizing or trimerizing the molecules as conventional in the art.

Further polypeptides of the present invention include polypeptides which have at least 93%, 95%, 96%, 97%, 98%, or 99% similarity to those described above. The polypeptides of the invention also contain those which are at least 93%, 94%, or 95%, 96%, 97%, 98%, or 99% identical to a polypeptide encoded by a nucleic acid sequence of the Sequence Listing.

The % similarity of two polypeptides can be measured by a similarity score determined by comparing the amino acid sequences of the two polypeptides using the Bestfit program with the default settings for determining similarity. Bestfit uses the local homology algorithm of Smith and Waterman, *Advances in Applied Mathematics* 2:482-489 (1981) to find the best segment of similarity between two sequences.

A polypeptide having an amino acid sequence at least, for example, 95% identical to a reference amino acid sequence of an SDF-1 polypeptide is one in which the amino acid sequence of the polypeptide is identical to the reference sequence except that the polypeptide sequence may include up to five amino acid alterations per each 100 amino acids of the reference polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids, up to 5% of the total amino acid residues in the reference sequence, may be inserted into the reference sequence. These alterations of the reference sequence may occur at the amino or carboxy terminal positions of the reference amino acid sequence or anywhere between those terminal positions, interspersed either individually among residues in the reference sequence, or in one or more contiguous groups within the reference sequence.

As a practical matter, whether any particular polypeptide is at least 93%, 95%, 96%, 97%, 98%, or 99% identical to, for instance, an amino acid sequence or to a polypeptide sequence encoded by a nucleic acid sequence set forth in the Sequence Listing can be determined conventionally using known computer programs, such the Bestfit program. When using Bestfit or other sequence alignment program to determine whether a particular sequence is, for instance, 95% identical to a reference sequence according to the present invention, the parameters are set, of course, that the percentage of identity is calculated over the full length of the reference amino acid sequence and that gaps in homology of up to 5% of the total number of amino acid residues in the reference sequence are allowed.

As described in detail below, the polypeptides of the present invention can be used to raise polyclonal and monoclonal antibodies, which are useful in assays for detecting SDF-1 protein expression, also as described below, or as agonists and/or antagonists capable of enhancing or inhibiting SDF-1 protein function. These polypeptides can also be used in a yeast two-hybrid system to capture SDF-1 protein binding proteins, which are also candidate agonists and antagonists, according to the present invention. The yeast two hybrid system is described in Fields and Song, *Nature*, 340: 245-246 (1989).

Aptamers

Another suitable agent for modulating an activity of a subject polypeptide is an aptamer. Aptamers of the invention include both nucleotide and peptide aptamers. Nucleotide aptamers of the invention include double stranded DNA and single stranded RNA molecules that bind to ADAM12 proteins or fragments thereof. Peptide aptamers are peptides or small polypeptides that act as dominant inhibitors of protein function. Peptide aptamers specifically bind to target proteins, blocking their functional ability (Kolonin et al., *Proc. Natl. Acad. Sci.* 95:14,266-14,271 (1998)).

Due to the highly selective nature of peptide aptamers, they can be used not only to target a specific protein, but also to target specific functions of a given protein (for example, a signaling function). Further, peptide aptamers can be expressed in a controlled fashion by use of promoters which regulate expression in a temporal, spatial, or inducible manner. Peptide aptamers act dominantly, therefore, they can be used to analyze proteins for which loss-of-function mutants are not available. Aptamers of the invention may bind nucleotide cofactors (Latham et al., *Nucl. Acids Res.* 22:2817-2822 (1994)).

Peptide aptamers that bind with high affinity and specificity to a target protein can be isolated by a variety of techniques known in the art. Peptide aptamers can be isolated from random peptide libraries by yeast two-hybrid screens (Xu et al., *Proc. Natl. Acad. Sci.* 94:12,473-12,478. (1997)). They can also be isolated from phage libraries (Hoogenboom et al., *Immunotechnology* 4:1-20 (1998)) or chemically generated peptides/libraries.

Epitope-Bearing Portions

In another aspect, the invention provides a polypeptide comprising an epitope-bearing portion of a polypeptide of the invention. The epitope of this polypeptide portion is an immunogenic or antigenic epitope of a polypeptide of the invention. Immunogenic epitopes are those parts of a protein that elicit an antibody response when the whole protein is provided as the immunogen. On the other hand, a region of a protein molecule to which an antibody can bind is an antigenic epitope. The number of immunogenic epitopes of a protein generally is less than the number of antigenic epitopes. See, for instance, Geysen et al., *Proc. Natl. Acad. Sci.*, USA 81:3998-4002 (1983).

As to the selection of polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe et al., *Science*, 219:660-666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful for raising antibodies, including monoclonal antibodies, that bind specifically to a polypeptide of the invention. See, for instance, Wilson et al., *Cell*, 37:767-778 (1984). The epitope-bearing peptides and polypeptides of the invention may be produced by any conventional means. See, for example, Houghten, *Proc. Natl. Acad. Sci.*, USA 82:5131-5135 (1985), and U.S. Pat. No. 4,631,211 (1986).

Epitope-bearing peptides and polypeptides of the invention can be used to induce antibodies according to methods well known in the art. See, for instance, Bittle, et al, *J. Gen. Virol.*, 66:2347-2354 (1985). Immunogenic epitope-bearing peptides of the invention, i.e., those parts of a protein that elicit an antibody response when the whole protein is the immunogen, are identified according to methods known in the art. See, for instance, U.S. Pat. No. 5,194,392 (1990), which describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 (1989) describes a method of detecting or determining a sequence of monomers which is a topographical equivalent of a ligand which is complementary to the ligand binding site of a particular receptor of interest. Similarly, U.S. Pat. No. 5,480,971 (1996) discloses linear C1-C7-alkyl peralkylated oligopeptides, and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, SDF-1 polypeptides of the present invention, and the epitope-bearing fragments thereof described above, can be combined with parts of the constant domain of immunoglobulins, resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins, for example, EP A 394,827; Traunecker et al., *Nature*, 331:84-86 (1988). Fusion proteins that have a disulfide-linked dimeric structure due to the IgG part can also be more efficient in binding and neutralizing other molecules than the monomeric SDF-1 protein or protein fragment alone, for example, as described by Fountoulakis et al., *J. Biochem.*, 270:3958-3964 (1995). Suitable chemical moieties for derivatization of a heterologous polypeptide include, for example, polymers, such as water soluble polymers, all or part of human serum albumin, fetuin A, fetuin B, leucine zipper nuclear factor erythroid derivative-2 (NFE2), neuroretinal leucine zipper, mannose motif (mbp1), tetranectin, and an Fc region.

Polymers, e.g., water soluble polymers, are useful in the present invention as the polypeptide to which each polymer is attached will not precipitate in an aqueous environment, such as a physiological environment. Polymers employed in the invention will be pharmaceutically acceptable for the preparation of a therapeutic product or composition. One skilled in the art will be able to select the desired polymer based on such considerations as whether the polymer/protein conjugate will be used therapeutically and, if so, the desired dosage, circulation time, and resistance to proteolysis.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone) polyethylene glycol, polypropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll, or dextran and mixtures thereof.

As used herein, polyethylene glycol (PEG) is meant to encompass any of the forms that have been used to derivatize other proteins, such as mono-(C1-C10) alkoxy- or aryloxy-polyethylene glycol. Polyethylene glycol propionaldehyde may have advantages in manufacturing due to its stability in water.

Specifically, a modified heterologous polypeptide of the invention may be prepared by attaching polyaminoacids or branch point amino acids to the polypeptide. For example, the polyaminoacid may be a carrier protein that serves to increase the circulation half life of the polypeptide (i.e., in addition to the advantages achieved via a fusion molecule). For the therapeutic purpose of the present invention, such polyaminoacids should ideally be those that have or do not create neutralizing antigenic response, or other adverse responses. Such polyaminoacids may be selected from serum album (such as human serum albumin), an additional antibody or portion thereof, for example the Fc region, fetuin A, fetuin B, leucine zipper nuclear factor erythroid derivative-2 (NFE2), neuroretinal leucine zipper, mannose motif (mbp1), tetranectin, or other polyaminoacids, e.g. lysines. As described herein, the location of attachment of the polyaminoacid may be at the N-terminus, or C-terminus, or other places in between, and also may be connected by a chemical "linker" moiety to the selected molecule.

Polymers used herein, for example water soluble polymers, may be of any molecular weight and may be branched or unbranched. The polymers each typically have an average molecular weight of between about 2 kDa to about 100 kDa (the term "about" indicating that in preparations of a polymer, some molecules will weigh more, some less, than the stated molecular weight). The average molecular weight of each polymer may be between about 5 kDa and about 50 kDa, or between about 12 kDa and about 25 kDa. Generally, the higher the molecular weight or the more branches, the higher the polymer:protein ratio. Other sizes may also be used, depending on the desired therapeutic profile; for example, the duration of sustained release; the effects, if any, on biological activity; the ease in handling; the degree or lack of antigenicity; and other known effects of a polymer on a modified molecule of the invention.

Polymers employed in the present invention are typically attached to a heterologous polypeptide with consideration of effects on functional or antigenic domains of the polypeptide. In general, chemical derivatization may be performed under any suitable condition used to react a protein with an activated polymer molecule. Activating groups which can be used to link the polymer to the active moieties include the following: sulfone, maleimide, sulfhydryl, thiol, triflate, tresylate, azidirine, oxirane, and 5-pyridyl.

Polymers of the invention are typically attached to a heterologous polypeptide at the alpha ($\alpha$) or epsilon ($\epsilon$) amino groups of amino acids or a reactive thiol group, but it is also contemplated that a polymer group could be attached to any reactive group of the protein that is sufficiently reactive to become attached to a polymer group under suitable reaction conditions. Thus, a polymer may be covalently bound to a heterologous polypeptide via a reactive group, such as a free amino or carboxyl group. The amino acid residues having a free amino group may include lysine residues and the N-terminal amino acid residue. Those having a free carboxyl group may include aspartic acid residues, glutamic acid residues, and the C-terminal amino acid residue. Those having a reactive thiol group include cysteine residues.

Methods for preparing fusion molecules conjugated with polymers, such as water soluble polymers, will each generally involve (a) reacting a heterologous polypeptide with a polymer under conditions whereby the polypeptide becomes attached to one or more polymers and (b) obtaining the reaction product. Reaction conditions for each conjugation may be selected from any of those known in the art or those subsequently developed, but should be selected to avoid or limit exposure to reaction conditions such as temperatures, solvents, and pH levels that would inactivate the protein to be modified. In general, the optimal reaction conditions for the reactions will be determined case-by-case based on known parameters and the desired result. For example, the larger the ratio of polymer:polypeptide conjugate, the greater the percentage of conjugated product. The optimum ratio (in terms of efficiency of reaction in that there is no excess unreacted polypeptide or polymer) may be determined by factors such as the desired degree of derivatization (e.g., mono-, di-tri-etc.), the molecular weight of the polymer selected, whether the polymer is branched or unbranched and the reaction conditions used. The ratio of polymer (e.g., PEG) to a polypeptide will generally range from 1:1 to 100:1. One or more purified conjugates may be prepared from each mixture by standard purification techniques, including among others, dialysis, salting-out, ultrafiltration, ion-exchange chromatography, gel filtration chromatography, and electrophoresis.

One may specifically desire an N-terminal chemically modified protein. One may select a polymer by molecular weight, branching, etc., the proportion of polymers to protein (polypeptide or peptide) molecules in the reaction mix, the type of reaction to be performed, and the method of obtaining the selected N-terminal chemically modified protein. The method of obtaining the N-terminal chemically modified protein preparation (i.e., separating this moiety from other mono-derivatized moieties if necessary) may be by purification of the N-terminal chemically modified protein material from a population of chemically modified protein molecules.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively attach a polymer to the N-terminus of the protein by performing the reaction at a pH which allows one to take advantage of the pKa differences between the $\epsilon$-amino group of the lysine residues and that of the $\alpha$-amino group of the N-terminal residue of the protein. By such selective derivatization, attachment of a polymer to a protein is controlled: the conjugation with the polymer takes place predominantly at the N-terminus of the protein and no significant modification of other reactive groups, such as the lysine side chain amino groups, occurs. Using reductive alkylation, the polymer may be of the type described above and should have a single reactive aldehyde for coupling to the protein. Polyethylene glycol propionaldehyde, containing a single reactive aldehyde, may also be used.

In one embodiment, the present invention contemplates the chemically derivatized polypeptide to include mono- or poly- (e.g., 2-4) PEG moieties. Pegylation may be carried out by any of the pegylation reactions known in the art. Methods for preparing a pegylated protein product will generally include (a) reacting a polypeptide with polyethylene glycol (such as a reactive ester or aldehyde derivative of PEG) under conditions whereby the protein becomes attached to one or more PEG groups; and (b) obtaining the reaction product(s). In general, the optimal reaction conditions for the reactions will be determined case by case based on known parameters and the desired result.

There are a number of PEG attachment methods available to those skilled in the art. See, for example, EP 0 401 384; Malik et al., *Exp. Hematol.,* 20:1028-1035 (1992); Francis, *Focus on Growth Factors,* 3(2):4-10 (1992); EP 0 154 316; EP 0 401 384; WO 92/16221; WO 95/34326; and the other publications cited herein that relate to pegylation, the disclosures of which are hereby incorporated by reference.

Additionally, heterologous polypeptides of the present invention and the epitope-bearing fragments thereof described herein can be combined with parts of the constant domain of immunoglobulins (IgG), resulting in chimeric polypeptides. These particular fusion molecules facilitate purification and show an increased half-life in vivo. This has been shown, e.g., for chimeric proteins consisting of the first two domains of the human CD4-polypeptide and various domains of the constant regions of the heavy or light chains of mammalian immunoglobulins, for example, EP A 394,827; Traunecker et al., *Nature,* 331:84-86 (1988). Fusion molecules that have a disulfide-linked dimeric structure due to the IgG part can also be more efficient in binding and neutralizing other molecules than, for example, a monomeric polypeptide or polypeptide fragment alone, see, for example, Fountoulakis et al., *J. Biochem.,* 270:3958-3964 (1995).

In another described embodiment, a human serum albumin fusion molecule may also be prepared as described herein and as further described in U.S. Pat. No. 6,686,179.

Moreover, the polypeptides of the present invention can be fused to marker sequences, such as a peptide that facilitates purification of the fused polypeptide. In preferred embodiments, the marker amino acid sequence is a hexa-histidine peptide such as the tag provided in a pQE vector (QIAGEN, Inc., among others, many of which are commercially available. As described in Gentz et al., *Proc. Natl. Acad. Sci. USA* 86:821-824 (1989), for instance, hexa-histidine provides for convenient purification of the fusion protein. Another peptide tag useful for purification, the chemagglutinin HA tag, corresponds to an epitope derived from the influenza hemagglutinin protein. (Wilson et al., *Cell* 37:767 (1984)).

Secretory Leader Sequences

As demonstrated herein, and in U.S. 60/647,013, in order for some secreted proteins to express and secrete in larger quantities, a secretory leader sequence from another, i.e., different, secreted protein is desirable. Employing heterologous secretory leader sequences is advantageous in that a resulting mature amino acid sequence, i.e., protein, of the secreted polypeptide is not altered as the secretory leader sequence is removed in the ER during the secretion process. Moreover, the addition of a heterologous secretory leader is often required to express and secrete, for example, extracellular domains of Type II single transmembrane proteins (STM), as the secretory leader, which is also a transmembrane spanning domain, must typically be removed so that they may be soluble.

Co-Translational and Post-Translational Modifications

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand. Any of numerous chemical modifications may be carried out by known techniques, including but not limited to specific chemical cleavage by cyanogen bromide, trypsin, chymotrypsin, papain, V8 protease; $NABH_4$; acetylation; formylation; oxidation; reduction; and/or metabolic synthesis in the presence of tunicamycin.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic, or affinity label to allow for detection and isolation of the protein.

Also provided by the invention are chemically modified derivatives of the polypeptides of the invention which may provide additional advantages such as increased solubility, stability, and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three, or more attached chemical moieties.

A polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Suitable for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Compositions

In some embodiments, SDF-1 compositions are provided in formulation with pharmaceutically acceptable excipients, a wide variety of which are known in the art (Gennaro, *Remington: The Science and Practice of Pharmacy with Facts and Comparisons: Drugfacts Plus,* 20th ed. (2003); Ansel et al., *Pharmaceutical Dosage Forms and Drug Delivery Systems,* 7$^{th}$ ed., Lippencott Williams and Wilkins (2004); Kibbe et al., *Handbook of Pharmaceutical Excipients,* 3$^{rd}$ ed., Pharmaceutical Press (2000)). Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In pharmaceutical dosage forms, the compositions of the invention can be administered in the form of their pharmaceutically acceptable salts, or they can also be used alone or in appropriate association, as well as in combination, with other pharmaceutically active compounds. The subject compositions are formulated in accordance to the mode of potential administration. Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid or gaseous forms, such as tablets, capsules, powders, granules, ointments, solutions, suppositories, enemas, injections, inhalants and aerosols. The following methods and excipients are merely exemplary and are in no way limiting.

Compositions for oral administration can form solutions, suspensions, tablets, pills, granules, capsules, sustained release formulations, oral rinses, or powders. For oral preparations, the agents, polynucleotides, and polypeptides can be used alone or in combination with appropriate additives, for example, with conventional additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art (Gennaro, 2003). The composition or formulation to be administered will, in any event, contain a quantity of the agent adequate to achieve the desired state in the subject being treated.

The agents, polynucleotides, and polypeptides can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Other formulations for oral or parenteral delivery can also be used, as conventional in the art.

The antibodies, agents, polynucleotides, and polypeptides can be utilized in aerosol formulation to be administered via inhalation. The compounds of the present invention can be formulated into pressurized acceptable propellants such as dichlorodifluoromethane, propane, nitrogen, and the like. Further, the agent, polynucleotides, or polypeptide composition may be converted to powder form for administration intranasally or by inhalation, as conventional in the art.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

A polynucleotide, polypeptide, or other modulator, can also be introduced into tissues or host cells by other routes, such as viral infection, microinjection, or vesicle fusion. For example, expression vectors can be used to introduce nucleic acid compositions into a cell as described above. Further, jet injection can be used for intramuscular administration (Furth et al., *Anal. Biochem.* 205:365-368 (1992)). The DNA can be coated onto gold microparticles, and delivered intradermally by a particle bombardment device, or "gene gun" as described in the literature (Tang et al., *Nature* 356:152-154 (1992)), where gold microprojectiles are coated with the DNA, then bombarded into skin cells.

Unit dosage forms for oral or rectal administration such as syrups, elixirs, and suspensions can be provided wherein each dosage unit, for example, teaspoonful, tablespoonful, tablet, or suppository, contains a predetermined amount of the composition containing one or more agents. Similarly, unit dosage forms for injection or intravenous administration can comprise the agent(s) in a composition as a solution in sterile water, normal saline or another pharmaceutically acceptable carrier.

Chromosome Assays

In certain embodiments relating to chromosomal mapping, a cDNA herein disclosed is used to clone the genomic nucleic acid of the SDF-1. This can be accomplished using a variety of well known techniques and libraries, which generally are commercially available. The genomic DNA then is used for in situ chromosome mapping using techniques well known for this purpose. Therefore, the nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase Chromosomal spread can be used to provide a precise chromosomal location in one step. This technique can be used with a cDNA as short as approximately 50-60 bases. For a review of this technique, see Verma et al., *Human Chromosomes: A Manual of Basic Techniques*, Pergamon Press, New York (1988).

Once a sequence has been mapped to a precise chromosomal location, the physical position of the sequence on the chromosome can be correlated with genetic map data. (Such data are found, for example, in V. McKusick, *Mendelian Inheritance in Man*, available on line through Johns Hopkins University Welch Medical Library). The relationship between genes and diseases that have been mapped to the same chromosomal region are then identified through linkage analysis (coinheritance of physically adjacent genes).

Next, differences can be determined in the cDNA or genomic sequences of affected and unaffected individuals. If a mutation is observed in some or all of the affected individuals but not in any normal individuals, then the mutation is likely to be the causative agent of the disease. With current resolution of physical mapping and genetic mapping techniques, a cDNA precisely localized to a chromosomal region associated with the disease could be one of between 50 and 500 potential causative genes (assuming 1 megabase mapping resolution and one gene per 20 kb).

Using methods described above, the SDF-1 gene of the invention has been mapped by fluorescent in situ hybridization to human chromosome 10q11.1. The corresponding map position in the mouse includes several disease loci, including whim syndrome, immunologic deficiency syndromes, HIV infections, inflammation, acquired immunodeficiency syndrome, B cell leukemias, chronic lymphocytic leukemia, metastasis, and rheumatoid arthritis (http://biostatpub2.mdanderson.org/cgi-bin/gene cards/carddisp?CXCL12&search=sdf-1&suff=txt).

Identification of Agonists and Antagonists

This invention provides modulators, i.e., polypeptides, polynucleotides, or other agents that increase or decrease the activity of their target. They may act as an agonist or antagonist, and interfere with the binding or activity of polypeptides or polynucleotides. Such modulators or agents include, for example, polypeptide variants, whether agonist or antagonist; antibodies, whether agonist or antagonist; soluble receptors, usually antagonists; small molecule drugs, whether agonist or antagonist; RNAi, usually an antagonist; antisense molecules, usually an antagonist; and ribozymes, usually an antagonist. In some embodiments, an agent is a subject polypeptide, where the subject polypeptide itself is administered to an individual. In some embodiments, an agent is an antibody specific for a subject "target" polypeptide. In some embodiments, an agent is a chemical compound such as a small molecule that may be useful as an orally available drug. Such modulation includes the recruitment of other molecules that directly effect the modulation. For example, an antibody that modulates the activity of a subject polypeptide that is a receptor on a cell surface may bind to the receptor and fix complement, activating the complement cascade and resulting in lysis of the cell. An agent which modulates a biological activity of a subject polypeptide or polynucleotide increases or decreases the activity or binding at least about 10%, at least about 15%, at least about 20%, at least about 25%, at least about 50%, at least about 80%, or at least about 2-fold, at least about 5-fold, or at least about 10-fold or more when compared to a suitable control.

This invention also provides a method of screening compounds to identify those which modulate the action of the polypeptide of the present invention. An example of such an assay comprises combining a mammalian fibroblast cell and the polypeptide(s) of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3$[H] thymidine in each case. The amount of fibroblast cell proliferation is measured by liquid scintillation chromatography, which measures the incorporation of $^3$[H] thymidine. Both agonistic and antagonistic compounds may be identified by this procedure.

In another method, a mammalian cell or membrane preparation expressing a receptor for a polypeptide of the present invention, as described above, is incubated with a labeled polypeptide of the present invention in the presence of the compound. The ability of the compound to enhance or block this interaction could then be measured. Alternatively, the response of a known second messenger system following interaction of a compound to be screened and the SDF-1 receptor is measured and the ability of the compound to bind to the receptor and elicit a second messenger response is measured to determine if the compound is a potential agonist or antagonist. Such second messenger systems include, but are not limited to, cAMP, guanylate cyclase, ion channels, and phosphoinositide hydrolysis.

Examples of antagonistic compounds include antibodies, or in some cases, oligonucleotides, which bind to a receptor of a polypeptide of the present invention but elicit no second messenger response, or which bind to the SDF-1 polypeptide itself. Alternatively, a potential antagonist may be a mutant form of the polypeptide which binds to the receptors but elicits no second messenger response, thus effectively blocking the action of the polypeptide.

Another compound antagonistic to SDF-1 genes and gene products is an antisense construct prepared using antisense technology. Antisense technology can be used to control gene expression through triple-helix formation or antisense DNA or RNA; both methods are based on the binding of a polynucleotide to DNA or RNA. For example, a 5' coding portion of the polynucleotide sequence, which encodes mature polypeptides of the present invention, can be used to design an antisense RNA oligonucleotide of from about 10 to about 40 base pairs in length. A DNA oligonucleotide is designed to be complementary to a region of the gene involved in transcription, for example, a triple helix—see Lee et al., *Nucl. Acids Res.*, 6:3073 (1979); Cooney et al, *Science*, 241:456 (1988); and Dervan et al., *Science*, 251: 1360 (1991), thereby preventing transcription and the production of the polypeptides of the present invention. The antisense RNA oligonucleotide hybridizes to the mRNA in vivo and blocks translation of the mRNA molecule into the polypeptide, as described by Okano, *J. Neurochem.*, 56:560 (1991); *Oligodeoxynucleotides as Antisense Inhibitors of Gene Expression*, CRC Press, Boca Raton, Fla. (1988). The oligonucleotides described above can also be delivered to cells such that the antisense RNA or DNA is expressed in vivo to inhibit polypeptide production.

Potential antagonist compounds also include small molecules which bind to and occupy the binding site of the receptors, thereby making the receptor inaccessible to its polypeptide such that normal biological activity is prevented. Examples of small molecules include, but are not limited to, small peptides or peptide-like molecules. Antagonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The present invention also provides methods for identifying agents, such as antibodies, which enhance or block the actions of SDF-1 molecules on cells. For example these agents may enhance or block interaction of SDF-1-binding molecules, such as receptors. Agents of interest include both agonists and antagonists. The invention provides agonists which increase the natural biological functions of SDF-1 or which function in a manner similar to SDF-1. The invention also provides antagonists, which decrease or eliminate the functions of SDF-1.

One method of identifying SDF-1 agonists and antagonists involves biochemical assays following subcellular fractionation. For example, a cellular compartment, such as a membrane or cytosolic preparation may be prepared from a cell that expresses a molecule that binds SDF-1 molecules, such as a molecule of a signaling or regulatory pathway modulated by SDF-1 molecules. Subcellular fractionation methods are known in the art of cell biology, and can be tailored to produce crude fractions with discrete and defined components, e.g., organelles or organellar membranes. The preparation is incubated with labeled SDF-1 molecules in the absence or the presence of a candidate molecule which may be an SDF-1 agonist or antagonist. The ability of the candidate molecule to interact with the binding molecule or an SDF-1 molecules is reflected in decreased binding of the labeled ligand. Molecules which bind gratuitously, that is, without inducing the effects of SDF-1 molecules, are most likely antagonists. Molecules that bind well and elicit effects that are the same as or closely related to SDF-1 molecules may potentially prove to be agonists.

The effects of potential agonists and antagonists may by measured, for instance, by determining an activity of one or more components of a second messenger system following interaction of the candidate molecule with a cell or appropriate cell preparation, and comparing the effect with that of SDF-1 molecules, or with that of molecules that elicit the same effects as SDF-1. Second messenger systems which may be useful in this regard include, but are not limited to, cAMP, cGMP, ion channel, and phosphoinositide hydrolysis second messenger systems.

Another example of an assay for the identification of SDF-1 antagonists is a competitive assay that combines a mixture of SDF-1 molecules and a potential antagonist, with membrane-bound SDF-1 receptor molecules. Under appropriate conditions for a competitive inhibition assay, this assay can also be performed with recombinant SDF-1 receptor molecules. SDF-1 molecules can be labeled, such as by radioactivity, such that the number of SDF-1 molecules bound to a receptor molecule can be determined accurately to assess the effectiveness of the potential antagonist.

Potential antagonists include small organic molecules, polypeptides, and antibodies that bind to a polypeptide of the invention, and thereby inhibit or extinguish its activity. Potential antagonists also may be small organic molecules, polypeptides such as closely related proteins or antibodies that bind the same sites on a binding molecule, such as a receptor molecule, without inducing SDF-1-induced activities, thereby preventing the action of SDF-1 molecules by excluding SDF-1 molecules from binding. Antagonists of the invention include fragments of the SDF-1 molecules having the nucleic acid and amino acid sequences shown in the Sequence Listing.

Other potential antagonists include antisense molecules. Antisense technology can be used to control gene expression through, e.g., antisense DNA or RNA, or through triple-helix formation. Antisense techniques are discussed, for example, in Okano, *J. Neurochem.*, 56:560 (1991); *Oligodeoxynucleotides as Antisense Inhibitors of Gene Expression*, CRC Press, Boca Raton, Fla. (1988). Triple helix formation is discussed in, for instance, Lee et al., *Nucleic Acids Research*, 6:3073 (1979); Cooney et al., *Science*, 241:456 (1988); and Dervan et al., *Science*, 251:1360 (1991). The methods are based on the binding of a polynucleotide to a complementary DNA or RNA. For example, the 5' coding portion of a polynucleotide that encodes the mature polypeptide of the present invention may be used to design an antisense RNA oligonucleotide of from about 10 to about 40 base pairs in length. A DNA oligonucleotide is designed to be complementary to a region of the gene involved in transcription, thereby preventing transcription and the subsequent production of SDF-1 molecules. The antisense RNA oligonucleotide hybridizes to the mRNA in vivo and blocks translation of the mRNA molecule into an SDF-1 polypeptide. The oligonucleotides described above can also be delivered to cells such that the antisense RNA or DNA may be expressed in vivo to inhibit production of SDF-1 molecules.

Therapeutic Uses of SDF-1 and its Agonists and Antagonists

SDF-1 polynucleotides, polypeptides, agonists, and/or antagonists of the invention may be used in developing treatments for any disorder mediated (directly or indirectly) by defective SDF-1 molecules, or insufficient amounts of either of these. SDF-1 polypeptides, agonists, and/or antagonists may be administered to a patient (e.g., a mammal, such as human) afflicted with such a disorder. Alternatively, a gene therapy approach may be applied to treat such disorders. Disclosure herein of SDF-1 nucleotide sequences permits the detection of defective SDF-1 genes, and the replacement thereof with normal SDF-1-encoding genes. Defective genes may be detected in in vitro diagnostic assays, and by comparison of the SDF-1 nucleotide sequences disclosed herein with that of an SDF-1 gene derived from a patient suspected of harboring a defect in this gene.

The SDF-1 molecules of the present invention may be employed to treat lymphoproliferative disease which results in lymphadenopathy. They may also mediate apoptosis by stimulating clonal deletion of T-cells and may, therefore, be employed to treat autoimmune disease to stimulate peripheral tolerance and cytotoxic T-cell mediated apoptosis. The SDF-1 molecules may further be employed as a research tool in elucidating the biology of autoimmune disorders, including systemic lupus erythematosus (SLE), Graves' disease, immunoproliferative disease lymphadenopathy (IPL), angio-immunoproliferative lymphadenopathy (AIL), immunoblastic lymphadenopathy (IBL), rheumatoid arthritis, diabetes, and multiple sclerosis. It also finds use in treating allergies and graft versus host disease.

The SDF-1 polynucleotides, polypeptides, and/or agonists or antagonists of the invention may also be used to treat, prevent, diagnose, and/or prognose diseases which include, but are not limited to, autoimmune disorders, immunodeficiency disorders, and graft versus host disease. Specific types of autoimmune diseases that can be treated with the molecules of the invention include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th-1 lymphocyte-related disorders (e.g., rheumatoid arthritis, multiple sclerosis, psoriasis, Sjögren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes).

The SDF-1 polypeptides of the present invention may be employed to inhibit neoplasia, such as tumor cell growth. They may be responsible for tumor destruction through apoptosis and cytotoxicity to certain cells.

Diseases associated with increased cell survival, or the inhibition of apoptosis, that may be treated, prevented, diagnosed and/or prognosed with the SDF-1 polynucleotides, polypeptides and/or agonists or antagonists of the invention include, but are not limited to, cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma, and ovarian cancer); autoimmune disorders (such as, multiple sclerosis, Sjögren's syndrome, Graves' disease, Hashimoto's thyroiditis, autoimmune diabetes, biliary cirrhosis, Behcet's disease, Crohn's disease, polymyositis, systemic lupus erythematosus, and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. SDF-1 polynucleotides and/or polypeptides, and their agonists, and/or antagonists may be used to inhibit growth, progression, and/or metastasis of cancers, in particular those listed above or in the paragraph that follows.

Additional diseases or conditions associated with increased cell survival, that may be treated, prevented, diagnosed, and/or prognosed with the SDF-1 polynucleotides and/or polypeptides and their agonists and/or antagonists include, but are not limited to, progression and/or metastases of malignancies and related disorders such as leukemia (including acute leukemias, (e.g., acute lymphocytic leukemia and acute myelocytic leukemia (including myeloblastic, promyelocytic, myelomonocytic, monocytic, and erythroleukemia) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenström's macroglobulinemia, heavy chain diseases, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis, that may be treated, prevented, diagnosed and/or prognosed with the SDF-1 polynucleotides, polypeptides and/or agonists or antagonists of the invention include, but are not limited to, AIDS, neurodegenerative disorders (such as Alzheimer's disease, Parkinson's disease, amyotrophic lateral sclerosis, retinitis pigmentosa, cerebellar degeneration, and brain tumor or prior associated disease); diabetes, autoimmune disorders (such as, multiple sclerosis, Sjögren's syndrome, Graves' disease, Hashimoto's thyroiditis, autoimmune diabetes, biliary cirrhosis, Behcet's disease, Crohn's disease, polymyositis, SLE, immune-related glomerulonephritis, autoimmune gastritis, thrombocytopenic purpura, and rheumatoid arthritis) myelodysplastic syndromes (such as aplastic anemia), graft vs. host disease (acute and/or chronic), ischemic injury (such as that caused by myocardial infarction, stroke, and reperfusion injury), liver injury or disease (e.g., hepatitis related liver injury, cirrhosis, ischemia/reperfusion injury, cholestosis (bile duct injury) and liver cancer); toxin-induced liver disease (such as that caused by alcohol), septic shock, ulcerative colitis, cachexia, and anorexia. In some embodiments, SDF-1 polynucleotides, polypeptides, agonists, and/or antagonists are used to treat the diseases and disorders listed above.

Molecules of the invention are useful for killing or inhibiting the multiplication of a cell that produces an infectious disease or for treating an infectious disease. The molecules of the invention can be used accordingly in a variety of settings for the treatment of an infectious disease in an animal. In the context of an infectious disease, the term "treating" includes any or all of preventing the growth, multiplication or replication of the pathogen that causes the infectious disease and ameliorating one or more symptoms of an infectious disease.

Many of the pathologies associated with HIV are mediated by apoptosis, including HIV-induced nephropathy and HIV encephalitis. Thus, in some embodiments, SDF-1 polynucleotides, polypeptides, agonists or antagonists of the invention are used to treat AIDS and pathologies associated with AIDS.

Another embodiment of the present invention is directed to the use of SDF-1 polynucleotides, polypeptides, or antagonists to reduce SDF-1-mediated death of T cells in HIV-infected patients. The role of T cell apoptosis in the development of AIDS has been the subject of a number of studies (see, for example, Meyaard et al., *Science*, 257:217-219 (1992); Groux et al., *J. Exp. Med.*, 175:331 (1992); and Oyaizu et al., in *Cell Activation and Apoptosis in HIV Infection*, Andrieu and Lu, Eds., Plenum Press, New York, pp. 101-114 (1995)). Fas-mediated apoptosis has been implicated in the loss of T cells in HIV positive individuals (Katsikis et al., *J. Exp. Med.* 181:2029-2036 (1995). It is also likely that T cell apoptosis occurs through multiple mechanisms.

Activated human T cells are induced to undergo programmed cell death (apoptosis) upon triggering through the CD3/T cell receptor complex, a process termed activated-induced cell death (AICD). AICD of CD4 T cells isolated from HIV-infected asymptomatic individuals has been reported (Groux et al., supra). Thus, AICD may play a role in the depletion of CD4+ T cells and the progression to AIDS in HIV-infected individuals. Thus, the present invention provides a method of inhibiting SDF-1-mediated T cell death in HIV patients, comprising administering SDF-1 polynucleotides, polypeptides, or antagonists of the invention to the patients. In one embodiment, the patient is asymptomatic when treatment with SDF-1 polynucleotides, polypeptides, or antagonists commences. If desired, prior to treatment, peripheral blood T cells may be extracted from an HIV patient, and tested for susceptibility to SDF-1-mediated cell death by procedures known in the art. In one embodiment, a patient's blood or plasma is contacted with SDF-1 antagonists (e g., anti-SDF-1 antibodies) of the invention ex vivo. The SDF-1 antagonists may be bound to a suitable chromatography matrix by procedures known in the art. The patient's blood or plasma flows through a chromatography column containing SDF-1 antagonist bound to the matrix, before being returned to the patient. The immobilized SDF-1 antagonist binds SDF-1, thus removing SDF-1 protein from the patient's blood.

In additional embodiments, an SDF-1 polynucleotide, polypeptide, or antagonist of the invention is administered in combination with other inhibitors of T cell apoptosis. For example, as discussed above, Fas-mediated apoptosis also has been implicated in loss of T cells in HIV individuals (Katsikis et al., *J. Exp. Med.*, 181:2029-2036 (1995)). Thus, a patient susceptible to both Fas ligand mediated and SDF-1-mediated T cell death may be treated with both an agent that blocks SDF-1/SDF-1 receptor interactions and an agent that blocks Fas-ligand/Fas interactions. Suitable agents for blocking binding of Fas-ligand to Fas include, but are not limited to, soluble Fas polypeptides; multimeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in WO 95/10540, hereby incorporated by reference.

In another example, agents which block binding of SDF-1 to an SDF-1 receptor are administered with the SDF-1 polynucleotides, polypeptides, or antagonists of the invention. Such agents include, but are not limited to, soluble SDF-1 receptor polypeptides; multimeric forms of soluble SDF-1 receptor polypeptides; and SDF-1 receptor antibodies that bind the SDF-1 receptor without transducing the biological signal that results in apoptosis, anti-SDF-1 antibodies that block binding of SDF-1 to one or more SDF-1 receptors, and muteins of SDF-1 that bind SDF-1 receptors but do not transduce the biological signal that results in apoptosis.

SDF-1 polypeptides of the invention may also be employed to regulate hematopoeisis and, in particular, erythropoiesis. Hematopoeisis is a multi-step cell proliferation and differentiation process which begins with a pool of multipotent stem cells. These cells can proliferate and differentiate into hematopoietic progenitors in reply to different stimuli. The SDF-1 polypeptides of the invention, as well as agonists and antagonists thereof, may be used to either stimulate or inhibit development of hematopoietic cells and, in particular, erythropoietic precursor cells.

SDF-1 may be used to treat B-cell deficiencies, including those arising in the context of infection, cancer treatment, transplant, immunodeficiency, immune disorder, agammaglobulinemia, hypogammaglobulinemia, defects in B cell development, defects in B cell function, defects in B-cell regulation, and shortened B cell lifespan. IL-7 is one of the factors involved in mediating B cell development (Stoddart et al., *Immunol. Rev.* 175:47-58 (2000)). Specifically, SDF-1 may be used to treat Bruton agammaglobulinemia, an X chromosome-linked agammaglobulinemia conventionally understood as a life-threatening disease that involves a failure in normal development of B lymphocytes and is associated with missense mutations in BTK, a gene encoding a cytoplasmic tyrosine kinase (Bruton agammaglobulinemia tyrosine kinase, EC 2.7.1.112), a member of the Tec family of protein-tyrosine kinases (Ohta et al., *Proc. Natl. Acad. Sci.* 91:9062-9066 (1994).

SDF-1 may be used to treat platelet deficiencies, such as manifest by thrombocytopenia. It can stimulate the growth and proliferation of lymphocytes, and can promote angiogenesis. SDF-1 is useful in the treatment of diabetes. It can modulate the immune response of an organism, can treat allergies, and can be used to treat and/or prevent infection. SDF-1 can inhibit tumor growth and can be used to treat cancer.

SDF-1 can treat or prevent ischemic disease. In an embodiment, the invention provides Additionally, molecules of the invention may be employed as agents to boost immunoresponsiveness among individuals having a temporary immune deficiency. Conditions resulting in a temporary immune deficiency that may be ameliorated or treated by administering the SDF-1 polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, and recovery from surgery.

In the context of an autoimmune disease, the term "treating" includes any or all of preventing replication of cells associated with an autoimmune disease state including, but not limited to, cells capable of producing an autoimmune antibody, lessening the autoimmune-antibody burden, and ameliorating one or more symptoms of an autoimmune disease.

SDF-1 polynucleotides or polypeptides of the invention, or agonists or antagonists thereof, may be used to diagnose, prognose, treat, or prevent one or more of the following diseases or disorders, or conditions associated therewith: primary immunodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, SDF-1 polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19, patients with stable multiple myeloma who are at high risk for infection (e.g., recurrent infection), autoimmune hemolytic anemia (e.g., warm-type autoimmune hemolytic anemia), thrombocytopenia (e.g., neonatal thrombocytopenia), and immune-mediated neutropenia), transplantation (e.g., cytomegalovirus (CMV)-negative recipients of CMV-positive organs), hypogammaglobulinemia (e.g., hypogammaglobulinemic neonates with risk factor for infection or morbidity), epilepsy (e.g., intractable epilepsy), systemic vasculitic syndromes, myasthenia gravis (e.g., decompensation in myasthenia gravis), dermatomyositis, and polymyositis.

Autoimmune disorders and conditions associated with these disorders that may be treated, prevented, and/or diagnosed with the SDF-1 polynucleotides, polypeptides, and/or antagonist of the invention (e.g., anti-SDF-1 antibodies), include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), multiple sclerosis, neuritis, uveitis ophthalmia, polyendocrinopathies, purpura (e.g., Henloch-Scoenlein purpura), Reiter's disease, stiff-man syndrome, autoimmune pulmonary inflammation, Guillain-Barre syndrome, insulin dependent diabetes mellitus, and autoimmune inflammatory eye disease.

Additional autoimmune disorders highly likely to be treated, prevented, and/or diagnosed with the compositions of the invention include, but are not limited to, autoimmune thyroiditis, hypothyroidism (i.e., Hashimoto's thyroiditis) (often characterized, e.g., by cell-mediated and humoral thyroid cytotoxicity), systemic lupus erythematosus (often characterized, e.g., by circulating and locally generated immune complexes), Goodpasture's syndrome (often characterized, e.g., by anti-basement membrane antibodies), pemphigus (often characterized, e.g., by epidermal acantholytic antibodies), receptor autoimmunities such as, for example, (a) Graves' disease (often characterized, e.g., by TSH receptor antibodies), (b) myasthenia gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized red blood cells), autoimmune thrombocytopenic purpura (often characterized, e.g., by phagocytosis of antibody-sensitized platelets.

Additional autoimmune disorders which may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone anti-nuclear antibodies), pernicious anemia (often characterized, e.g., by antibodies to parietal cells, microsomes, and intrinsic factor), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes) such as primary glomerulonephritis and IgA nephropathy, bullous pemphigoid (often characterized, e.g., by IgG and complement in the basement membrane), Sjögren's syndrome (often characterized, e.g., by multiple tissue antibodies, and/or a specific nonhistone anti-nuclear antibodies (SS-B)), diabetes mellitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Further autoimmune disorders which may be treated, prevented, and/or diagnosed with the compositions of the invention include, but are not limited to, chronic active hepatitis (often characterized, e.g. by smooth muscle antibodies), primary biliary cirrhosis (often characterized, e.g., by mitochondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-myocardial infarction (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), inflammatory myopathies, and many other inflammatory, granulamatous, degenerative, and atrophic disorders.

In an additional embodiment, SDF-1 polynucleotides or polypeptides, or antagonists thereof (e.g., anti-SDF-1 antibodies) are used to treat or prevent systemic lupus erythematosus and/or diseases, disorders or conditions associated therewith. Lupus-associated diseases, disorders, or conditions that may be treated or prevented with SDF-1 polynucleotides or polypeptides, or antagonists of the invention, include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleuricy)), renal disorders (e.g., nephritis), neurological disorders (e.g., seizures, peripheral neuropathy, CNS related disorders), gastrointestinal disorders, Raynaud phenomenon, and pericarditis.

SDF-1 polypeptides, agonists, or antagonists of the invention may be used to treat diseases associated with ischemia, e.g., cardiovascular disorders, including peripheral artery disease, such as limb ischemia. They may also include stroke, vascular disease, and fulminant liver failure. In the context of an ischemic disease, the term "treating" includes any or all of preventing the growth, multiplication, or replication of the pathogen that causes the ischemic disease and ameliorating one or more symptoms of an ischemic disease.

Stem cell mobilization to the heart and differentiation into cardiac myocytes is a naturally occurring process. Askari et al., *Lancet* 362:697-703 (2005), have speculated that up-regulation of this process can help recover myocardial function following infarction. In an embodiment, SDF-1 induces therapeutic stem cell homing to injured myocardium. SDF-1 has been observed to be up-regulated following myocardial infarction (Askari et al., supra). The invention provides compositions and methods for providing SDF-1 to the heart. For example, autologous cells genetically modified with molecules of the Sequence Listing can be transplanted to a subject that can benefit from such cells. Bone marrow stimulation may be performed in conjunction with the transplantation. Cardiac fibroblasts and cardiac myoblasts can be transfected with SDF-1 as described by Askari et al., supra, or other means known in the art, and provided in vivo by local administration. A rodent model with a ligation of the left anterior descending artery is suitable for studying and practicing this method. The method is suitable for therapeutic purposes in humans. This method of promoting tissue regeneration may be accomplished by stem cell engraftment. It is applicable to the heart, and other organs, including the brain, pancreas, lung, liver, skin, and bone. SDF-1 can be delivered to the tissues by conventional local administration of a molecule described herein or a composition comprising such molecule. SDF-1 can also be delivered to the tissues by local administration of a cell comprising a molecule described herein or a composition comprising such molecule. Suitable cells include heart cells, brain cells, pancreatic cells, lung cells, liver cells, skin cells, bone cells, mesenchymal stem cells, progenitor cells, adult stem cells, and embryonic stem cells.

Cardiovascular disorders include cardiovascular abnormalities, such as arterio-arterial fistula, arteriovenous fistula, cerebral arteriovenous malformations, congenital heart defects, pulmonary atresia and scimitar syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of Fallot, transposition of great vessels, double outlet right ventricle, tricuspid atresia, persistent truncus arteriosus, and heart septal defects, such as aortopulmonary septal defect, endocardial cushion defects, Lutembacher's syndrome, trilogy of Fallot, and ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, scimitar syndrome, cardiovascular syphilis, and cardiovascular tuberculosis.

Arrhythmias include sinus arrhythmia, atrial fibrillation, atrial flutter, bradycardia, extrasystole, Adams-Stokes syndrome, bundle-branch block, sinoatrial block, long QT syndrome, parasystole, Lown-Ganong-Levine syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve diseases include aortic valve insufficiency, aortic valve stenosis, heart murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau disease, Klippel-Trenaunay-Weber syndrome, Sturge-Weber syndrome, angioneurotic edema, aortic diseases, Takayasu's arteritis, aortitis, Leriche's syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, ataxia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subarachnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thromboses include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's syndrome, Churg-Strauss syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Additionally, ocular disorders associated with neovascularization which can be treated with the SDF-1 polynucleotides and polypeptides of the present invention (including SDF-1 agonists and SDF-1 antagonists) include, but are not limited to neovascular glaucoma, diabetic retinopathy, retinoblastoma, retrolental fibroplasia, uveitis, retinopathy of prematurity, macular degeneration, corneal graft neovascularization, as well as other eye inflammatory diseases, ocular tumors, and diseases associated with choroidal or iris neovascularization. See, e.g., reviews by Waltman et al., *Am. J. Ophthal.*, 85:704-710 (1978) and Gartner et al., *Surv. Ophthal.*, 22:291-312 (1978).

Additionally, disorders which can be treated with the SDF-1 polynucleotides and polypeptides of the present invention (including SDF-1 agonists and SDF-1 antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Polynucleotides and/or polypeptides of the invention, and/ or agonists and/or antagonists thereof, are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the Jung, stomach cancer, etc.), lymphoproliferative disorders (e.g., lymphadenopathy), microbial (e.g., viral, bacterial, etc.) infection (e.g., HIV-1 infection, HIV-2 infection, herpes virus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococci, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/ or agonists and/or antagonists thereof are useful in promoting angiogenesis, wound healing (e.g., wounds, burns, and bone fractures).

Polynucleotides and/or polypeptides of the invention and/ or agonists and/or antagonists thereof are also useful as an adjuvant to enhance immune responsiveness to specific antigen and/or anti-viral immune responses.

More generally, polynucleotides and/or polypeptides of the invention and/or agonists and/or antagonists thereof are useful in regulating (i.e., elevating or reducing) the immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or otherwise known in the art.

The uses of the SDF-1 polypeptides, include, but are not limited to, the treatment or prevention of viral hepatitis, herpes viral infections, allergic reactions, adult respiratory distress syndrome, neoplasia, anaphylaxis, allergic asthma, allergen rhinitis, drug allergies (e.g., to penicillin, cephalosporins), primary central nervous system lymphoma (PCNSL), glioblastoma, chronic lymphocytic leukemia (CLL), lymphadenopathy, autoimmune disease, graft versus host disease, rheumatoid arthritis, osteoarthritis, Graves' disease, acute lymphoblastic leukemia (ALL), lymphomas (Hodgkin's disease and non-Hodgkin's lymphoma (NHL)), opthalmopathy, uveoretinitis, the autoimmune phase of Type 1 diabetes, myasthenia gravis, glomerulonephritis, autoimmune hepatological disorder, autoimmune inflammatory bowel disease, and Crohn's disease. In addition, the SDF-1 polypeptides of the present invention may be employed to inhibit neoplasia, such as tumor cell growth. The combination of SDF-1 protein with immunotherapeutic agents such as IL-2 or IL-12 may result in synergistic or additive effects that would be useful for the treatment of established cancers.

Antibodies

SDF-1-protein specific antibodies for use in the present invention can be raised against the intact SDF-1 protein or an antigenic polypeptide fragment thereof. The protein or fragment may be presented with or without a carrier protein, such as an albumin, to an animal system (such as rabbit or mouse); in general the polypeptide fragments are sufficiently immunogenic to produce a satisfactory immune response without a carrier if they are at least about 25 amino acids in length.

Antibodies of the invention include polyclonal and monoclonal antibody preparations, as well as preparations including hybrid antibodies, altered antibodies, chimeric antibodies and, humanized antibodies, as well as: hybrid (chimeric) antibody molecules (see, for example, Winter et al., *Nature* 349:293-299 (1991)); and U.S. Pat. No. 4,816,567); F(ab')$_2$ and F(ab) fragments; Fv molecules (noncovalent heterodimers, see, for example, Inbar et al., *Proc. Natl. Acad. Sci.* 69:2659-2662 (1972)); and Ehrlich et al. (1980) *Biochem* 19:4091-4096); single-chain Fv molecules (sFv) (see, e.g., Huston et al., *Proc. Natl. Acad. Sci.* 85:5879-5883 (1980)); dimeric and trimeric antibody fragment constructs; minibodies (see, e.g., Pack et al., *Biochem.* 31:1579-1584 (1992); Cumber et al., *J. Immunology* 149B:120-126 (1992)); humanized antibody molecules (see, e.g., Riechmann et al, *Nature* 332:323-327 (1988); Verhoeyan et al, *Science* 239:1534-

1536 (1988)); and any functional fragments obtained from such molecules, wherein such fragments retain specific binding.

Methods of making monoclonal and polyclonal antibodies are known in the art. Monoclonal antibodies are generally antibodies having a homogeneous antibody population. The term is not limited regarding the species or source of the antibody, nor is it intended to be limited by the manner in which it is made. The term encompasses whole immunoglobulins. Polyclonal antibodies are generated by immunizing a suitable animal, such as a mouse, rat, rabbit, sheep or goat, with an antigen of interest, such as a stem cell transformed with a gene encoding an antigen. In order to enhance immunogenicity, the antigen can be linked to a carrier prior to immunization. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the antigen may be conjugated to a bacterial toxoid, such as toxoid from diphtheria, tetanus, cholera, etc., in order to enhance the immunogenicity thereof.

In addition, techniques developed for the production of chimeric antibodies (Morrison et al., *Proc. Natl. Acad. Sci.,* 81:851-855 (1984); Neuberger et al., *Nature,* 312:604-608 (1984); Takeda et al., *Nature,* 314:452-454 (1985)) by splicing genes from a mouse antibody molecule of appropriate antigen specificity together with genes from a human antibody molecule of appropriate biological activity can be used. Chimeric antibodies, i.e., antibodies in which different portions are derived from different animal species, such as those having a variable region derived from a murine monoclonal antibody and a human immunoglobulin constant region, for example, humanized antibodies, and insertion/deletions relating to cdr and framework regions, re suitable for use in the invention.

The invention also includes humanized antibodies, i.e., those with mostly human immunoglobulin sequences. Humanized antibodies of the invention generally refer to non-human immunoglobulins that have been modified to incorporate portions of human sequences. A humanized antibody may include a human antibody that contains entirely human immunoglobulin sequences.

The antibodies of the invention may be prepared by any of a variety of methods. For example, cells expressing the SDF-1 protein or an antigenic fragment thereof can be administered to an animal in order to induce the production of sera containing polyclonal antibodies. A preparation of SDF-1 protein can be prepared and purified to render it substantially free of natural contaminants, and the preparation introduced into an animal in order to produce polyclonal antisera with specific binding activity.

Antibodies of the invention specifically bind to their respective antigen(s); they may display high avidity and/or high affinity to a specific polypeptide, or more accurately, to an epitope of an antigen. Antibodies of the invention may bind to one epitope, or to more than one epitope. They may display different affinities and/or avidities to different epitopes on one or more molecules. When an antibody binds more strongly to one epitope than to another, adjusting the binding conditions can, in some instances, result in antibody binding almost exclusively to the specific epitope and not to any other epitopes on the same polypeptide, and not to a polypeptide that does not comprise the epitope.

The invention also provides monoclonal antibodies and SDF-1 protein binding fragments thereof. Monoclonal antibodies of the invention can be prepared using hybridoma technology, for example, Kohler et al., *Nature,* 256:495 (1975); Kohler et al., *Eur. J. Immunol.,* 6:511 (1976); Kohler et. al., *Eur. J. Immunol.,* 6:292 (1976); Hammerling et al., in: *Monoclonal Antibodies and T-Cell Hybridomas,* Elsevier, N.Y., (1981) pp. 563-681). In general, such procedures involve immunizing an animal (e.g., a mouse) with an SDF-1 protein antigen or with an SDF-1 protein-expressing cell. Suitable cells can be recognized by their capacity to bind anti-SDF-1 protein antibody. Such cells may be cultured in any suitable tissue culture medium; e.g., in Earle's modified Eagle's medium supplemented with 10% fetal bovine serum (inactivated at about 56° C.), and supplemented with about 10 grams/liter of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; e.g., the parent myeloma cell line (SP20), available from the American Type Culture Collection, Manassas, Va. After fusion, the resulting hybridoma cells are selectively maintained in HAT medium, and then cloned by limiting dilution as described by Wands et al., *Gastroenterology,* 80:225-232 (1981).

SDF-1 and SDF-1 Protein Antigen

Alternatively, antibodies capable of binding to the SDF-1 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, SDF-1-protein specific antibodies are used to immunize an animal, e.g., a mouse. The splenocytes of such an animal are then used to produce hybridoma cells, and the hybridoma cells are screened to identify clones which produce an antibody whose ability to bind to the SDF-1 protein-specific antibody can be blocked by the SDF-1 protein antigen. Such antibodies comprise anti-idiotypic antibodies to the SDF-1 protein-specific antibody and can be used to immunize an animal to induce formation of further SDF-1 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, SDF-1 protein-binding fragments can be produced through the application of recombinant DNA technology or through synthetic chemistry. Humanized chimeric monoclonal antibodies are suitable for in vivo use of anti-SDF-1 in humans. Such humanized antibodies can be produced using genetic constructs derived from hybridoma cells producing the monoclonal antibodies described above. Methods for producing chimeric antibodies are known in the art. See, for review, Morrison, *Science,* 229:1202 (1985); Oi et al., *BioTechniques,* 4:214 (1986); Cabilly et al., U.S. Pat. No. 4,816,567; Taniguchi et al., EP 171496; Morrison et al, EP 173494; Neuberger et al, WO 8601533; Robinson et al., WO 8702671; Boulianne et al., *Nature,* 312:643 (1984); Neuberger et al., *Nature,* 314:268 (1985).

Diagnosis

This invention is also related to the use of the genes of the present invention as part of a diagnostic assay for detecting diseases or susceptibility to diseases related to the presence of mutations in the nucleic acid sequences encoding the polypeptide of the present invention. Individuals carrying mutations in a gene of the present invention may be detected at the DNA level by a variety of techniques. Nucleic acids for diagnosis may be obtained from a patient's cells, such as from blood, urine, saliva, tissue biopsy, and autopsy material. The genomic DNA may be used directly for detection or may be amplified enzymatically by using PCR, for example, as described by Saiki et al., *Nature,* 324: 163-166 (1986), prior to analysis. RNA or cDNA may also be used for the same purpose. As an example, PCR primers complementary to the nucleic acid encoding a polypeptide of the present invention can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Genetic testing based on DNA sequence differences may be achieved by detecting alterations in electrophoretic mobility of DNA fragments in gels run with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures, for example, as described by Myers et al., *Science,* 230:1242 (1985).

Sequence changes at specific locations may also be revealed by nuclease protection assays, such as RNase and S1 protection or the chemical cleavage method as shown in Cotton et al., *Proc. Natl. Acad. Sci.,* USA, 85:4397-4401 (1985). Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA. In addition to more conventional gel-electrophoresis and DNA sequencing, mutations can also be detected by in situ analysis.

The present invention also relates to a diagnostic assay for detecting altered levels of SDF-1 proteins in various tissues. An over-expression of these proteins compared to normal control tissue samples may detect the presence of abnormal cellular proliferation, for example, a tumor. Assays used to detect protein levels in a host-derived sample are well-known to those of skill in the art and include radioimmunoassays, competitive-binding assays, Western Blot analysis, ELISA assays, "sandwich" assays, and other assays for the expression levels of the genes encoding the SDF-1 proteins known in the art. Expression can be assayed by qualitatively or quantitatively measuring or estimating the level of SDF-1 protein, or the level of mRNA encoding SDF-1 protein, in a biological sample. Assays may be performed directly, for example, by determining or estimating absolute protein level or mRNA level, or relatively, by comparing the SDF-1 protein or mRNA to a second biological sample. In performing these assays, the SDF-1 protein or mRNA level in the first biological sample is measured or estimated and compared to a standard SDF-1 protein level or mRNA level; suitable standards include second biological samples obtained from an individual not having the disorder of interest. Standards may be obtained by averaging levels of SDF-1 in a population of individuals not having a disorder related to SDF-1 expression. As will be appreciated in the art, once a standard SDF-1 protein level or mRNA level is known, it can be used repeatedly as a standard for comparison.

An ELISA assay, for example, as described by Coligan, et al., *Current Protocols in Immunology,* 1(2), Chap. 6, (1991), utilizes an antibody prepared with specificity to a polypeptide antigen of the present invention. In addition, a reporter antibody is prepared against the monoclonal antibody. To the reporter antibody is attached a detectable reagent such as a radioactive tag, a fluorescent tag, or an enzymatic tag, e.g., a horseradish peroxidase. A sample is removed from a host and incubated on a solid support, e.g. a polystyrene dish, that binds the proteins in the sample. Any free protein binding sites on the dish are then covered by incubating with a non-specific protein, e.g., bovine serum albumin. Next, the specific antibody, e.g., a monoclonal antibody, is incubated in the dish, during which time the antibody attaches to any polypeptides of the present invention attached to the polystyrene dish. All unbound monoclonal antibody is washed out with buffer. The reporter antibody, i.e., one linked to horseradish peroxidase is placed in the dish, resulting in the binding of the reporter antibody to any antibody bound to the protein of interest; unattached reporter antibody is then removed. Substrate, e.g., peroxidase, is then added to the dish, and the amount of signal produced color, e.g., developed in a given time period provides a measurement of the amount of a polypeptide of the present invention present in a given volume of patient sample when compared against a standard.

A competition assay may be employed wherein antibodies specific to a polypeptide of the present invention are attached to a solid support, and labeled SDF-1, along with a sample derived from the host, are passed over the solid support. The label can be detected and quantified, for example, by liquid scintillation chromatography, and the measurement can be correlated to the quantity of the polypeptide of interest present in the sample. A "sandwich" assay, similar to an ELISA assay, may be employed, wherein a polypeptide of the present invention is passed over a solid support and binds to antibody modules attached to the solid support. A second antibody is then bound to the polypeptide of interest. A third antibody, which is labeled and specific to the second antibody is then passed over the solid support and binds to the second antibody. The amount of antibody binding can be quantified; it correlates with the amount of the polypeptide of interest.

Biological samples of the invention can include any biological sample obtained from a subject, body fluid, cell line, tissue culture, or other source which contains SDF-1 protein or mRNA. As indicated, biological samples include body fluids (such as sera, plasma, urine, synovial fluid, and spinal fluid) which contain free SDF-1 protein, ovarian or renal system tissue, and other tissue sources found to express complete or mature SDF-1 polypeptide or an SDF-1 receptor. Methods for obtaining tissue biopsies and body fluids from mammals are well known in the art. Where the biological sample is to include mRNA, a tissue biopsy may provide the source.

Total cellular RNA can be isolated from a biological sample using any suitable technique such as the single-step guanidinium-thiocyanate-phenol-chloroform method described in Chomczynski and Sacchi, *Anal. Biochem.,* 162: 156-159 (1987). Levels of mRNA encoding the SDF-1 protein are then assayed using any appropriate method. These include Northern blot analysis, S1 nuclease mapping, PCR, reverse transcription in combination with PCR (RT-PCR), and reverse transcription in combination with the ligase chain reaction (RT-LCR).

Assaying SDF-1 protein levels in a biological sample can be performed using antibody-based techniques. For example, SDF-1 protein expression in tissues can be studied with classical immunohistological methods, for example, Jalkanen, M., et al., *J. Cell. Biol.*, 101:976-985 (1985); Jalkanen, M., et al, *J. Cell. Biol.*, 105:3087-3096 (1987). Other antibody-based methods useful for detecting SDF-1 protein gene expression include immunoassays, such as the enzyme linked immunosorbent assay (ELISA) and the radioimmunoassay (RIA). Suitable antibody assay labels are known in the art and include enzyme labels, such as glucose oxidase, radioisotopes, and fluorescent labels, such as fluorescein and rhodamine, and biotin.

In addition to assaying SDF-1 protein levels in a biological sample obtained from an individual, SDF-1 protein can also be detected in vivo by imaging. Antibody labels or markers for in vivo imaging of SDF-1 protein include those detectable by X-radiography, NMR, or ESR. For X-radiography, suitable labels include radioisotopes such as barium or cesium, which emit detectable radiation but are not overtly harmful to a subject. Suitable markers for NMR and ESR include those with a detectable characteristic spin, such as deuterium, which may be incorporated into the antibody by labeling of nutrients for the relevant hybridoma.

An SDF-1 protein-specific antibody or antibody fragment which has been labeled with an appropriate detectable imaging moiety, such as a radioisotope, a radio-opaque substance, or a material detectable by nuclear magnetic resonance, is introduced, for example, parenterally, subcutaneously or intraperitoneally, into the subject to be examined for an immune system disorder. It will be understood in the art that the size of the subject and the imaging system used will determine the quantity of imaging moiety needed to produce diagnostic images. The labeled antibody or antibody fragment will then preferentially accumulate at the location of cells which contain SDF-1 protein. In vivo tumor imaging is described in Burchiel et al., ed., Chapter 13, *Tumor Imaging: The Radiochemical Detection of Cancer*, Masson Publishing Inc. (1982).

Formulations

The SDF-1 polypeptide compositions will be formulated and dosed in a fashion consistent with good medical practice, taking into account the clinical condition of the individual subject, the site of delivery of the SDF-1 polypeptide composition, the method of administration, the scheduling of administration, and other factors known to practitioners. The effective amount of SDF-1 polypeptide for purposes herein is thus determined by such considerations.

The polypeptides, agonists, and antagonists of the present invention may be employed in combination with a suitable pharmaceutical carrier to comprise a pharmaceutical composition for parenteral administration. Such compositions comprise a therapeutically effective amount of the polypeptide, agonist, or antagonist and a pharmaceutically acceptable carrier or excipient. Such a carrier includes, but is not limited to, saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The pharmaceutical compositions may be administered in a convenient manner such as by the oral, topical, intravenous, intraperitoneal, intramuscular, subcutaneous, intranasal, or intradermal routes. The pharmaceutical compositions are administered in an amount which is effective for treating and/or prophylaxis of the specific indication. In general, they are administered in an amount of at least about 10 micrograms/kg body weight and in most cases they will be administered in an amount not in excess of about 8 milligrams/kg body weight per day.

The polypeptides of the invention, and agonist and antagonist compounds which are polypeptides, may also be employed in accordance with the present invention by expression of such polypeptides in vivo, i.e., gene therapy. Thus, for example, cells may be engineered with a polynucleotide (DNA or RNA) encoding for the polypeptide ex vivo; the engineered cells are then provided to a patient. Such methods are well-known in the art. For example, cells may be engineered by procedures known in the art by use of a retroviral particle containing RNA encoding for the polypeptide of the present invention.

Similarly, cells may be engineered in vivo for expressing the polypeptide in vivo, for example, by procedures known in the art. As known in the art, a cell producing a retroviral particle containing RNA encoding the polypeptide of the present invention may be administered to a patient for the purpose of engineering cells in vivo and expressing the polypeptide in vivo. These and other methods for administering a polypeptide of the present invention by similar methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney Murine Leukemia virus, spleen necrosis virus, retroviruses such as Rous sarcoma virus, Harvey sarcoma virus, avian leukosis virus, gibbon ape leukemia virus, human immunodeficiency virus, adenovirus, myeloproliferative sarcoma virus, and mammary tumor virus. In one embodiment, the retroviral plasmid vector is derived from Moloney murine leukemia virus.

The nucleic acid sequence encoding the polypeptide of the present invention is under the control of a suitable promoter. Vectors of the invention include one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980-990 (1989), or any other homologous or heterologous promoter, for example, cellular promoters such as eukaryotic cellular promoters including, but not limited to, the histone, pol III, and β-actin promoters. Other viral promoters which may be employed include, but are not limited to, adenovirus promoters, e.g., the adenoviral major late promoter; thymidine kinase (TK) promoters; and B19 parvovirus promoters.

Suitable promoters include the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the beta-actin promoter; and human growth hormone promoters. The promoter also may be the native promoter which controls the gene encoding the polypeptide. The selection of a suitable promoter will be apparent to those skilled in the art from the teachings contained herein.

A retroviral plasmid vector can be employed to transduce packaging cell lines to form producer cell lines. Examples of packaging cells which may be transfected include, but are not limited to, the PE501, PA317, -2, -AM, PA12, T19-14X, VT-19-17-H2, CRE, CRIP, GP+E-86, GP+envAm12, and DAN cell lines as described in Miller, *Human Gene Therapy*, 1:5-14 (1990). The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

SDF-1 "Knock-Outs" and Homologous Recombination

Endogenous gene expression can be reduced by inactivating or "knocking out" a gene of interest and/or its promoter using targeted homologous recombination. (e.g., see Smithies et al., *Nature*, 317:230-234 (1985); Thomas & Capecchi, *Cell*, 51:503-512 (1987); Thompson et al., *Cell*, 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express, the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (see, e.g., Thomas & Capecchi (1987) supra; Thompson (1989), supra). However, this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and/or vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and secretion, of the polypeptides of the invention. The engineered cells which express and secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic Non-Human Animals

The polypeptides of the invention can also be expressed in transgenic animals. Animals of any species, including, but not limited to, mice, rats, rabbits, hamsters, guinea pigs, pigs, micro-pigs, goats, sheep, cows, and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce a founder lines of transgenic animals. Such techniques include, but are not limited to, pronuclear microinjection (Paterson et al., *Appl. Microbial. Biotechnol.* 40:691-698 (1994); Carver et al., *Biotechnology* (NY) 11: 1263-1270 (1993); Wright et al., *Biotechnology* (NY) 9:830-834 (1991); and Hoppe et al., U.S. Pat. No. 4,873,191 (1989)); retrovirus mediated gene transfer into germ lines (Van der Putten et al., *Proc. Natl. Acad. Sci.*, USA 82:6148-6152 (1985)), blastocysts or embryos; gene targeting in embryonic stem cells (Thompson et al., *Cell* 56:313-321 (1989)); electroporation of cells or embryos (Lo, *Mol. Cell. Biol.* 3:1803-1814 (1983)); introduction of the polynucleotides of the invention using a gene gun (see, e.g., Ulmer et al., *Science* 259:1745 (1993); introducing nucleic acid constructs into embryonic pluripotent stem cells and transferring the stem cells back into the blastocyst; and sperm-mediated gene transfer (Lavitrano et al., *Cell* 57:717-723 (1989); etc. For a review of such techniques, see Gordon, *Intl. Rev. Cytol.* 115:171-229 (1989), which is incorporated by reference herein in its entirety. Further, the contents of each of the documents recited in this paragraph is herein incorporated by reference in its entirety. See also, U.S. Pat. No. 5,464,764 (Capecchi et al., Positive-Negative Selection Methods and Vectors); U.S. Pat. No. 5,631,153 (Capecchi et al., Cells and Non-Human Organisms Containing Predetermined Genomic Modifications and Positive-Negative Selection Methods and Vectors for Making Same); U.S. Pat. No. 4,736,866 (Leder et al., Transgenic Non-Human Animals); and U.S. Pat. No. 4,873,191 (Wagner et al., Genetic Transformation of Zygotes); each of which is hereby incorporated by reference in its entirety. Any technique known in the art may be used to produce transgenic clones containing polynucleotides of the invention, for example, nuclear transfer into enucleated oocytes of nuclei from cultured embryonic, fetal, or adult cells induced to quiescence (Campbell et al., Nature 380:64-66 (1996); Wilmut et al., Nature 385:810-813 (1997)), each of which is herein incorporated by reference in its entirety).

The present invention provides for transgenic animals that carry the transgene in all their cells, as well as animals which carry the transgene in some, but not all their cells, i.e., mosaic or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Proc. Natl. Acad. Sci. USA 89:6232-6236 (1992)). The regulatory sequences required for such a cell-type specific activation will depend upon the particular cell type of interest, and will be apparent to those of skill in the art. It may be desired that the polynucleotide transgene be integrated into the chromosomal site of the endogenous gene, gene targeting is then suitable. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Science 265:103-106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of SDF-1 polypeptides, studying conditions and/or disorders associated with aberrant SDF-1 expression, and in screening for compounds effective in ameliorating such conditions and/or disorders.

Kits

The present invention provides kits that can be used in the above methods. In one embodiment, a kit comprises an antibody of the invention, e.g., a purified antibody, in one or more containers. In a specific embodiment, the kits of the present invention contain a substantially isolated polypeptide comprising an epitope which is specifically immunoreactive with an antibody included in the kit. The kits of the present invention may also comprise a control antibody which does not react with the polypeptide of interest.

In another embodiment, the kits of the present invention comprise a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In embodiments, the kit may include a recombinantly produced or chemically synthesized polypeptide antigen. The polypeptide antigen of the kit may also be attached to a solid support.

In a further embodiment, the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In an embodiment, the antibody is a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined.

Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plates and/or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

All publications, patents and patent applications cited herein, whether supra or infra, are hereby incorporated by reference in their entirety.

As used in this specification and the appended claims, the singular forms "a," "an," and "the" include plural referents unless the content clearly dictates otherwise. Thus, for example, reference to "an antigen" includes a mixture of two or more antigens, a reference to "a subject polypeptide" includes a plurality of such polypeptides, and reference to "the agent" includes reference to one or more agents and equivalents thereof known to those skilled in the art, and so forth.

It will be clear that the invention may be practiced otherwise than as particularly described in the foregoing description and examples. Numerous modifications and variations of the present invention are possible in light of the above teachings and, therefore, are within the scope of the appended claims.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claim.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques.

Nonetheless, the numerical values set forth in the specific examples are reported as precisely as possible. Any numerical value, however, inherently contains certain errors from the standard deviation of its experimental measurement.

Patents and publications cited are incorporated by reference herein in their entireties; references cited in such publications are also incorporated by reference in their entireties.

Tables

TABLE 1

SEQ ID NOS.: 1-23

| FP ID | SEQ. ID. NO.: (N1) | SEQ. ID. NO.: (P1) | SEQ. ID. NO.: (N0) | Source ID |
|---|---|---|---|---|
| HG1015480 | SEQ. ID. NO.: 1 | SEQ. ID. NO.: 9 | SEQ. ID. NO.: 17 | CLN00235738_5pv1.a |
| HG1015481 | SEQ. ID. NO.: 2 | SEQ. ID. NO.: 10 | SEQ. ID. NO.: 18 | 18093693 |
| HG1015482 | SEQ. ID. NO.: 3 | SEQ. ID. NO.: 11 | SEQ. ID. NO.: 19 | NP_000600:NM_000609 |
| HG1015483 | SEQ. ID. NO.: 4 | SEQ. ID. NO.: 12 | SEQ. ID. NO.: 20 | 1220364:1220363 |
| HG1015484 | SEQ. ID. NO.: 5 | SEQ. ID. NO.: 13 | SEQ. ID. NO.: 21 | 10334450:1220365 |
| HG1015509 | SEQ. ID. NO.: 6 | SEQ. ID. NO.: 14 | | CLN00235738_5pv1.a_exon2-4 |
| HG1015510 | SEQ. ID. NO.: 7 | SEQ. ID. NO.: 15 | | CLN00235738_5pv1.a_exon3-4 |
| HG1015511 | SEQ. ID. NO.: 8 | SEQ. ID. NO.: 16 | | CLN00235738_5pv1.a_exon4 |
| HG1015522 | | SEQ. ID. NO.: 22 | | CLN00235738_5pv1.a_3p_region |
| HG1015525 | | SEQ. ID. NO.: 23 | | CLN00235738_5pv1.a_5p_region |

TABLE 2

ANNOTATION OF POLYPEPTIDE SEQUENCES

| FP ID | Source ID | Pred Prot Len | Top Human Hit Accession ID | Top Human Hit Annot | Top Human Hit % ID | Top Human Match Length |
|---|---|---|---|---|---|---|
| HG1015480 | CLN00235738_5pv1.a | 140 | gi\|10334450\|emb\|CAC10202.1\| | bA20J15.1.2 (stromal cell-derived factor 1, isoform beta) [Homo sapiens] | 100 | 92 |
| HG1015481 | 18093693 | 119 | gi\|10334450\|emb\|CAC10202.1\| | bA20J15.1.2 (stromal cell-derived factor 1, isoform beta) [Homo sapiens] | 100 | 92 |
| HG1015482 | NP_000600:NM_000609 | 93 | gi\|10834988\|ref\|NP_000600.1\| | chemokine (C—X—C motif) ligand 12 (stromal cell-derived factor 1); stromal cell-derived factor 1 [Homo sapiens] | 100 | 93 |

TABLE 2-continued

ANNOTATION OF POLYPEPTIDE SEQUENCES

| FP ID | Source ID | Pred Prot Len | Top Human Hit Accession ID | Top Human Hit Annot | Top Human Hit % ID | Top Human Match Length |
|---|---|---|---|---|---|---|
| HG1015483 | 1220364: 1220363 | 89 | gi\|1220364\|gb\|AAB39333.1\| | pre-B cell stimulating factor homologue | 100 | 89 |
| HG1015484 | 10334450: 1220365 | 92 | gi\|10334450\|emb\|CAC10202.1\| | bA20J15.1.2 (stromal cell-derived factor 1, isoform beta) [Homo sapiens] | 100 | 92 |
| HG1015509 | CLN00235738_5pv1.a_exon2-4 | 119 | gi\|10334450\|emb\|CAC10202.1\| | bA20J15.1.2 (stromal cell-derived factor 1, isoform beta) [Homo sapiens] | 56 | 92 |
| HG1015510 | CLN00235738_5pv1.a_exon3-4 | 80 | | no_human_hit | | |
| HG1015511 | CLN00235738_5pv1.a_exon4 | 51 | | no_human_hit | | |
| HG1015522 | CLN00235738_5pv1.a_3p_region | 21 | | no_human_hit | | |

TABLE 3

CHARACTERISTICS OF POLYPEPTIDE SEQUENCES

| FP ID | Source ID | Cluster | Class | Pred Prot Len | Tree vote | Mature Protein Coords | Signal Peptide Coords | Alternate Mature Protein Coords | TM | Pfam |
|---|---|---|---|---|---|---|---|---|---|---|
| HG1015480 | CLN00235738_5pv1.a | | | 140 | 0.98 | (22-140) | (1-21) | | 0 | IL8 |
| HG1015481 | 18093693 | | | 119 | 0.98 | (22-119) | (1-21) | | 0 | IL8 |
| HG1015482 | NP_000600: NM_000609 | 180496 | SECR | 93 | 1 | (22-93) | (1-21) | | 0 | IL8 |
| HG1015483 | 1220364:1220363 | 180496 | SECR | 89 | 0.98 | (22-89) | (1-21) | | 0 | IL8 |
| HG1015484 | 10334450:1220365 | 180496 | SECR | 92 | 0.98 | (22-92) | (1-21) | | 0 | IL8 |
| HG1015509 | CLN00235738_5pv1.a_exon2-4 | | | 119 | 0.21 | (1-119) | | | 0 | IL8 |
| HG1015510 | CLN00235738_5pv1.a_exon3-4 | | | 80 | 0.05 | (1-80) | | | 0 | IL8 |
| HG1015511 | CLN00235738_5pv1.a_exon4 | | | 51 | 0.08 | (1-51) | (27-51) | (12-26) | 0 | no_pfam |
| HG1015522 | CLN00235738_5pv1.a_3p_region | | | 21 | 0.09 | (1-21) | (7-20) | (21-21) | 0 | no_pfam |

TABLE 4

COMPARISON OF THE POLYPEPTIDES OF THE SEQUENCE LISTING WITH KNOWN POLYPEPTIDE SEQUENCES

| FP ID | Source ID | Pred Prot Len | Length of Match between FP ID and Source ID | % ID of FP ID vs Source ID over Length of FP ID | % ID of FP ID vs Source ID over Length of Source ID |
|---|---|---|---|---|---|
| HG1015480 | CLN00235738_5pv1.a | 140 | — | — | — |
| HG1015481 | 18093693 | 119 | 91 | 65% | 76% |
| HG1015482 | NP_000600:NM_000609 | 93 | 88 | 63% | 95% |
| HG1015483 | 1220364:1220363 | 89 | 88 | 63% | 99% |
| HG1015484 | 10334450:1220365 | 92 | 88 | 63% | 96% |
| HG1015509 | CLN00235738_5pv1.a_exon2-4 | 119 | — | — | — |
| HG1015510 | CLN00235738_5pv1.a_exon3-4 | 80 | — | — | — |
| HG1015511 | CLN00235738_5pv1.a_exon4 | 51 | — | — | — |
| HG1015522 | CLN00235738_5pv1.a_3p_region | 21 | — | — | — |

TABLE 5

PFAM COORDINATES

| FP ID | Source ID | Pfam | Coords. |
|---|---|---|---|
| HG1015480 | CLN00235738_5pv1.a | IL8 | (22-87) |
| HG1015481 | 18093693 | IL8 | (22-87) |
| HG1015482 | NP_000600:NM_000609 | IL8 | (22-87) |
| HG1015483 | 1220364:1220363 | IL8 | (22-87) |
| HG1015484 | 10334450:1220365 | IL8 | (22-87) |
| HG1015509 | CLN00235738_5pv1.a_exon2-4 | IL8 | (1-66) |
| HG1015510 | CLN00235738_5pv1.a_exon3-4 | IL8 | (1-27) |
| HG1015511 | CLN00235738_5pv1.a_exon4 | no_pfam | |
| HG1015522 | CLN00235738_5pv1.a_3p_region | no_pfam | |

Sequence Listing

SEQ.ID.NO. 1
HG1015480N1 CLN00235738_5pv1.a
ATGAACGCCAAGGTCGTGGTCGTGCTGGTCCTCGTGCTGACCGCGCTCTG
CCTCAGCGACGGGAAGCCCGTCAGCCTGAGCTACAGATGCCCATGCCGAT
TCTTCGAAAGCCATGTTGCCAGAGCCAACGTCAAGCATCTCAAAATTCTC
AACACTCCAAACTGTGCCCTTCAGATTGTAGCCCGGCTGAAGAACAACAA
CAGACAAGTGTGCATTGACCCGAAGCTAAAGTGGATTCAG
GAGTACCTGGAGAAAGCTTTAAACAACCTGATCAGCGCCGCACCAGCCGG
GAAGAGGGTG
ATTGCTGGGGCTCGTGCCCTGCATCCCTCTCCTCCCAGGGCCTGCCCCAC
AGCTCGGGCCCTCTGTGAGATCCGTCTTTGGCCTCCTCCAGAATGGAGCT
GGCCCTCTCCTGGGGATGTGTAA

SEQ.ID.NO. 2
HG1015481N1 18093693
ATGAACGCCAAGGTCGTGGTCGTGCTGGTCCTCGTGCTGACCGCGCTCTG
CCTCAGCGACGGGAAGCCCGTCAGCCTGAGCTACAGATGCCCATGCCGAT
TCTTCGAAAGCCATGTTGCCAGAGCCAACGTCAAGCATCTCAAAATTCTC
AACACTCCAAACTGTGCCCTTCAGATTGTAGCCCGGCTGAAGAACAACAA
CAGACAAGTGTGCATTGACCCGAAGCTAAAGTGGATTCAG
GAGTACCTGGAGAAAGCTTTAAACAAGGGGCGCAGAGAAGAAAAAGTGGG
GAAAAAGAA
AAGATAGGAAAAAGAAGCGACAGAAGAAGAGAAAGGCTGCCCAGAAAAG
GAAAAACTAG

SEQ.ID.NO. 3
HG1015482N1 NP_000600: NM_000609
ATGAACGCCAAGGTCGTGGTCGTGCTGGTCCTCGTGCTGACCGCGCTCTG
CCTCAGCGACGGGAAGCCCGTCAGCCTGAGCTACAGATGCCCATGCCGAT
TCTTCGAAAGCCATGTTGCCAGAGCCAACGTCAAGCATCTCAAAATTCTC
AACACTCCAAACTGTGCCCTTCAGATTGTAGCCCGGCTGAAGAACAACAA
CAGACAAGTGTGCATTGACCCGAAGCTAAAGTGGATTCAG
GAGTACCTGGAGAAAGCTTTAAACAAGAGGTTCAAGATGTGA

SEQ.ID.NO. 4
HG1015483N1 1220364: 1220363
ATGAACGCCAAGGTCGTGGTCGTGCTGGTCCTCGTGCTGACCGCGCTCTG
CCTCAGCGACGGGAAGCCCGTCAGCCTGAGCTACAGATGCCCATGCCGAT
TCTTCGAAAGCCATGTTGCCAGAGCCAACGTCAAGCATCTCAAAATTCTC
AACACTCCAAACTGTGCCCTTCAGATTGTAGCCCGGCTGAAGAACAACAA
CAGACAAGTGTGCATTGACCCGAAGCTAAAGTGGATTCAG
GAGTACCTGGAGAAAGCTTTAAACAAGTAA

SEQ.ID.NO. 5
HG1015484N1 10334450: 1220365
ATGAACGCCAAGGTCGTGGTCGTGCTGGTCCTCGTGCTGACCGCGCTCTG
CCTCAGCGACGGGAAGCCCGTCAGCCTGAGCTACAGATGCCCATGCCGAT
TCTTCGAAAGCCATGTTGCCAGAGCCAACGTCAAGCATCTCAAAATTCTC
AACACTCCAAACTGTGCCCTTCAGATTGTAGCCCGGCTGAAGAACAACAA
CAGACAAGTGTGCATTGACCCGAAGCTAAAGTGGATTCAG
GAGTACCTGGAGAAAGCTTTAAACAAGAGGTTCAAGATGTGA

SEQ.ID.NO. 6
HG1015509N1 CLN00235738_5pv1.a_exon2-4
AAGCCCGTCAGCCTGAGCTACAGATGCCCATGCCGATTCTTCGAAAGCCA
TGTTGCCAGAGCCAACGTCAAGCATCTCAAAATTCTCAACACTCCAAACT
GTGCCCTTCAGATTGTAGCCCGGCTGAAGAACAACAACAGACAAGTGTGC
ATTGACCCGAAGCTAAAGTGGATTCAGGAG
TACCTGGAGAAAGCTTTAAACAACCTGATCAGCGCCGCACCAGCCGGGAA
GAGGGTGATTGCTGGGGCTCGTGCCCTGCATCCCTCTCCTCCCAGGGCCT
GCCCCACAGCTCGGGCCCTCTGTGAGATCCGTCTTTGGCCTCCTCCAGAA
TGGAGCTGGCCCTCTCCTGGGGATGTGTAA SEQ.ID.NO. 7
HG1015510N1 CLN00235738_5pv1.a_exon3-4
GCCCGGCTGAAGAACAACAACAGACAAGTGTGCATTGACCCGAAGCTAAA
GTGGATTCAG
GAGTACCTGGAGAAAGCTTTAAACAACCTGATCAGCGCCGCACCAGCCGG
GAAGAGGGTG
ATTGCTGGGGCTCGTGCCCTGCATCCCTCTCCTCCCAGGGCCTGCCCCAC
AGCTCGGGCCCTCTGTGAGATCCGTCTTTGGCCTCCTCCAGAATGGAGCT
GGCCCTCTCCTGGGGATGTGTAA SEQ.ID.NO. 8
HG1015511N1 CLN00235738_5pv1.a_exon4
CTGATCAGCGCCGCACCAGCCGGGAAGAGGGTGATTGCTGGGGCTCGTGC
CCTGCATCCCTCTCCTCCCAGGGCCTGCCCCACAGCTCGGGCCCTCTGTG
AGATCCGTCTTTGGCCTCCTCCAGAATGGAGCTGGCCCTCTCCTGGGGAT
GTGTAA SEQ.ID.NO. 9
HG1015480P1 CLN00235738_5pv1.a
MNAKVVVVLVLVLTALCLSDGKPVSLSYRCPCRFFESHVARANVKHLKIL
NTPNCALQIVARLKNNNRQVCIDPKLKWIQEYLEKALNNLISAAPAGKRV
IAGARALHPSPPRACPTARALCEIRLWPPPEWSWPSPGDV SEQ.ID.NO. 10
HG1015481P1 18093693
MNAKVVVVLVLVLTALCLSDGKPVSLSYRCPCRFFESHVARANVKHLKIL
NTPNCALQIVARLKNNNRQVCIDPKLKWIQEYLEKALNKGRREEKVGKKE
KIGKKKRQKKRKAAQKRKN SEQ.ID.NO. 11
HG1015482P1 NP_000600: NM_000609
MNAKVVVVLVINLTALCLSDGKPVSLSYRCPCRFFESHVARANVKHLKIL
NTPNCALQIVARLKNNNRQVCIDPKLKWIQEYLEKALNKRFKM SEQ.ID.NO. 12
HG1015483P1 1220364: 1220363
MNAKVVVVLVLVLTALCLSDGKPVSLSYRCPCRFFESHVARANVKHLKIL
NTPNCALQIVARLKNNNRQVCIDPKLKWIQEYLEKALNK SEQ.ID.NO. 13
HG1015484P1 10334450: 1220365
MNAKVVVLVLVLTALCLSDGKPVSLSYRCPCRFFESHVARANVKHLKIL

NTPNCALQIVARLKNNNRQVCIDPKLKWIQEYLEKALNKFKM

SEQ.ID.NO. 14
HG1015509P1 CLN00235738_5pv1.a_exon2-4
KPVSLSYRCPCRFEESHVARANVKHLKILNTPNCALQIVARLKNNNRQVC

IDPKLKWIQEYLEKALNNLISAAPAGKRVIAGARALHPSPPRACPTARAL

CEIRLWPPPEWSWPSPGDV

SEQ.ID.NO. 15
HG1015510P1 CLN00235738_5pv1.a_exon3-4
ARLKNNNRQVCIDPKLKWIQEYLEKALNNLISAAPAGKRVIAGARALHPS

PPRACPTARALCEIRLWPPPEWSWPSPGDV

SEQ.ID.NO. 16
HG1015511P1 CLN00235738_5pv1.a_exon4
LISAAPAGKRVIAGARALHPSPPRACPTARALCEIRLWPPPEWSWPSPGD

V

SEQ.ID.NO. 17
HG1015480N0 CLN00235738_5pv1.a
ACTATAGAACCAGGCCGCACTTTCACTCTCCGTCAGCCGCATTGCCCGCT

CGGCGTCCGGCCCCCGACCCGCGCTCGTCCGCCCGCCCGCCCGCCCGCCC

GCGCCATGAACGCCAAGGTCGTGGTCGTGCTGGTCCTCGTGCTGACCGCG

CTCTGCCTCAGCGACGGGAAGCCCGTCAGCCTGAGCTACAGATGCCCATG

CCGATTCTTCGAAAGCCATGTTGCCAGAGCCAACGTCAAGCATCTCAAAA

TTCTCAACACTCCAAACTGTGCCCTTCAGATTGTAGCCCGGCTGAAGAAC

AACAACAGACAAGTGTGCATTGACCCGAAGCTAAAGTGGATTCAGGAGTA

CCTGGAGAAA

GCTTTAAACAACCTGATCAGCGCCGCACCAGCCGGGAAGAGGGTGATTGC

TGGGGCTCGTGCCCTGCATCCCTCTCCTCCCAGGGCCTGCCCCACAGCTC

GGGCCCTCTGTGAGATCCGTCTTTGGCCTCCTCCAGAATGGAGCTGGCCC

TCTCCTGGGATGTGTAATGGTCCCCCTGCTTACCCGCAAAAGACAAGTC

TTTACAGAATCAAATGCAATTTTAAATCTGAGAGCTCGCTTTGAGTGACT

GGGTTTTGTGATTGCCTCTGAAGCCTATGTATGCCATGGAGGCACTAACA

AACTCTGAGGTTTCCGAAATCAGAAGCGAAAAAATCAGTGAATAAACCAT

CATCTTGCCACTACCCCCTCCTGAAGCCACAGCAGGG

SEQ.ID.NO. 18
HG1015481N0 18093693
TATAGAACCAGAGCGCACTTTCACTCTCCGTCAGCCGCATTGCCCGCTCG

GCGTCCGGCCCCCGACCCGCGCTCGTCCGCCCGCCCGCCCGCCCGCCCGC

GCCATGAACGCCAAGGTCGTGGTCGTGCTGGTCCTCGTGCTGACCGCGCT

CTGCCTCAGCGACGGGAAGCCCGTCAGCCTGAGCTACAGATGCCCATGCC

GATTCTTCGAAAGCCATGTTGCCAGAGCCAACGTCAAGCATCTCAAAATT

CTCAACACTCCAAACTGTGCCCTTCAGATTGTAGCCCGGCTGAAGAACAA

CAACAGACAAGTGTGCATTGACCCGAAGCTAAAGTGGATTCAGGAGTACC

TGGAGAAAGC

TTTAAACAAGGGGCGCAGAGAAGAAAAAGTGGGGAAAAAAGAAAAGATAG

GAAAAAAGAA

GCGACAGAAGAAGAGAAAGGCTGCCCAGAAAAGGAAAAACTAGTTATCTG

CCACCTCGAG

ATGGACCACAGTTCACTTGCTCTCGGCGCTTTGTAAATTTGCTCGATCCT

CCTCCAGGACAGACCCCCATGCAGACTGGGCAGGGGCTCAGACTTCCGTG

GGGGAGCAGTGCTTTGCTGCCCTGCCAGCCACACCGGCTTCTGTATTTAT

GTGCTTTTTAAGGCCCTTGTTGGTCTGCTAAGTTATGAAGAAAGTAGTTG

TGCAGAGACTGGGCGGGGGTCTGTGACGCGGAGCCTGTGTGCTCAGGAC

TCTGTCCAGAATAGCCTGGGA

SEQ.ID.NO. 19
HG1015482N0 NP_000600: NM_000609
CGCGGCCGCAGCCGCATTGCCCGCTCGGCGTCCGGCCCCCGACCCGCGCT

CGTCCGCCCGCCCGCCCGCCCGCGCCATGAACGCCAAGGTCGTGGT

CGTGCTGGTCCTCGTGCTGACCGCGCTCTGCCTCAGCGACGGGAAGCCCG

TCAGCCTGAGCTACAGATGCCCATGCCGATTCTTCGAAAGCCATGTTGCC

AGAGCCAACGTCAAGCATCTCAAAATTCTCAACACTCCAAACTGTGCCCT

TCAGATTGTAGCCCGGCTGAAGAACAACAACAGACAAGTGTGCATTGACC

CGAAGCTAAAGTGGATTCAGGAGTACCTGGAGAAAGCTTTAAACAAGAGG

TTCAAGATGTGAGAGGGTCAGACGCCTGAGGAACCCTTACAGTAGGAGTC

CAGCTCTGAAACCAGTGTTAGGGAAGGGCCTGCCACAGCCTCCCCTGCCA

GGGCAGGGCCCCAGGCATTGCCAAGGGCTTTGTTTTGGACACTTTGCCAT

ATTTTTCACCATTGAATTATGTAGCAAAATACATGACATTTATTTTTCATT

TAGTTTGATTATTCAGTGTCACTGGCGACACGTAGCAGCTTAGACTAAGG

CCATTATTGTACTTGCCTTATTAGAGTGTCTTTCCACGGAGCCACTCCTC

TGACTCAGGGCTCCTGGGTTTTGGATTCTCTGAGCTGTGCAGGTGGGGAG

ACTGGGCTGAGGGAGCCTGGCCCCATGGTCAGCCCTAGGGTGGAGAGCCA

CCAAGAGGGACGCCTGGGGGTGTCAGGACC

AGTCAACCTGGGCAAAGCCTAGTGAAGGCTTCTCTCTGTGGGATGGGATG

GTGGAGGGCCACATGGGAGGTTCACCCCCT

SEQ.ID.NO. 20
HG1015483N0 1220364: 1220363
TCTCCGTCAGCCGCATTGCCCGCTCGGCGTCCGGCCCCCGACCCGTGCTC

GTCCGCCCGCCCGCCCGCCCGCGCCATGAACGCCAAGGTCGTGGTC

GTGCTGGTCCTCGTGCTGACCGCGCTCTGCCTCAGCGACGGGAAGCCCGT

CAGCCTGAGCTACAGATGCCCATGCCGATTCTTCGAAAGCCATGTTGCCA

GAGCCAACGTCAAGCATCTCAAAATTCTCAACACTCCAAACTGTGCCCTT

CAGATTGTAGCCCGGCTGAAGAACAACAACAGACAAGTGTGCATTGACCC

GAAGCTAAAGTGGATTCAGGAGTACCTGGAGAAAGCTTTAAACAAGTAAG

CACAACAGCC

AAAAAGGACTTTCCGCTAGACCCACTCGAGGAAAACTAAAACCTTGTGAG

AGATGAAAGG

GCAAAGACGTGGGGGAGGGGGCCTTAACCATGAGGACCAGGTGTGTGTGT

GGGGTGGGCA

CATTGATCTGGGATCGGGCCTGAGGTTTGCAGCATTTAGACCCTGCATTT

ATAGCATACGGTATGATATTGCAGCTTATATTCATCCATGCCCTGTACCT

GTGCACGTTGGAACTTTTATTACTGGGGTTTTTCTAAGAAAGAAATTGTA

TTATCAACAGCATTTTCAAGCAGTTAGTTCCTTCATGATCATCACAATCA

TCATCATTCTCATTCTCATTTTTTAAATCAACGAGTACTTCAAGATCTGA

ATTTGGCTTGTTTGGAGCATCTCCTCTGCTCCCCTGGGGAGTCTGGGCAC

AGTCAGGTGGTGGCTTAACAGGGAGCTGGAAAAAGTGTCCTTTCTTCAGA

CACTGAGGCTCCCGCAGCA

SEQ.ID.NO. 21
HG1015484N0 10334450: 1220365
TCTCCGTCAGCCGCATTGCCCGCTCGGCGTCCGGCCCCCGACCCGTGCTC

GTCCGCCCGCCCGCCCGCCCGCGCCATGAACGCCAAGGTCGTGGTC

GTGCTGGTCCTCGTGCTGACCGCGCTCTGCCTCAGCGACGGGAAGCCCGT

CAGCCTGAGCTACAGATGCCCATGCCGATTCTTCGAAAGCCATGTTGCCA

GAGCCAACGTCAAGCATCTCAAAATTCTCAACACTCCAAACTGTGCCCTT

CAGATTGTAGCCCGGCTGAAGAACAACAACAGACAAGTGTGCATTGACCC

GAAGCTAAAGTGGATTCAGGAGTACCTGGAGAAAGCTTTAAACAAGAGGT

TCAAGATGTGAGAGGGTCAGACGCCTGAGGAACCCTTACAGTAGGAGCCC

AGCTCTGAAACCAGTGTTAGGGAAGGGCCTGCCACAGCCTCCCCTGCCAG

GGCAGGGCCCCAGGCATTGCCAAGGGCTTTGTTTTGCACACTTTGCCATA

TTTTCACCATTTGATTATGTAGCAAAATACATGACATTTATTTTTCATTT

AGTTTGATTATTCAGTGTCACTGGCGACACGTAGCAGCTTAGACTAAGGC

CATTATTGTACTTGCCTTATTAGAGTGTCTTTCCACGGAGCCACTCCTCT

GACTCAGGGCTCCTGGGTTTTGTATTCTCTGAGCTGTGCAGGTGGGGAGA

CTGGGCTGAGGGAGCCTGGCCCCATGGTCAGCCCTAGGGTGGAGAGCCAC

CAAGAGGGACGCCTGGGGGTGCCAGGACCA

GTCAACCTGGGCAAAGCCTAGTGAAGGCTTCTCTCTGTGGGATGGGATGG

TGGAGGGCCACATGGGAGGCTCACCCCCT

SEQ.ID.NO. 22
HG1015522P1 CLN00235738_5pv1.a_3p_region
ALCEIRLWPPPEWSWPSPGDV

SEQ.ID.NO. 23
HG1015525P1 CLN00235738_5pv1.a_5p_region
MNAKVVVVLVLVLTALCLSDGKPVSLSYRCPCRFFESHVARANVKHLKIL
NTPNCALQIVARLKNNNRQVCIDPKLKWIQEYLEKALNN

---

The invention claimed is:

1. An isolated antibody that specifically binds to a polypeptide wherein the amino acid sequence of the polypeptide consists of the amino acid sequence set forth in SEQ ID NO:14.

2. The antibody of claim 1, wherein the antibody is a monoclonal antibody.

3. The antibody of claim 1, wherein the antibody is a polyclonal antibody.

4. The antibody of claim 1, wherein the antibody is an antibody fragment.

5. The antibody of claim 4, wherein the antibody fragment is an F(ab), F(ab')$_2$, or Fv fragment.

6. The antibody of claim 1, wherein the antibody is a humanized antibody.

7. The antibody of claim 1, wherein the antibody is a human antibody.

8. The antibody of claim 1, wherein the antibody is a chimeric antibody.

9. The antibody of claim 1, wherein the antibody is a bi-specific antibody.

* * * * *

SEQUENCE LISTING

<160> NUMBER OF SEQ ID NOS: 25

<210> SEQ ID NO 1
<211> LENGTH: 423
<212> TYPE: DNA
<213> ORGANISM: Homo sapiens

<400> SEQUENCE: 1
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
agagccaacg tcaagcatct caaaattctc aacactccaa actgtgccct tcagattgta     180
gcccggctga agaacaacaa cagacaagtg tgcattgacc cgaagctaaa gtggattcag     240
gagtacctgg agaaagcttt aaacaacctg atcagcgccg caccagccgg aagagggtg      300 attgctgggg ctcgtgccct gcatccctct cctcccaggg cctgccccac agctcgggcc     360
ctctgtgaga tccgtctttg gcctcctcca gaatggagct ggccctctcc tggggatgtg     420
taa                                                                   423

<210> SEQ ID NO 2
<211> LENGTH: 360
<212> TYPE: DNA
<213> ORGANISM: Homo sapiens

<400> SEQUENCE: 2
atgaacgcca aggtcgtggt cgtgctggtc ctcgtgctga ccgcgctctg cctcagcgac      60
gggaagcccg tcagcctgag ctacagatgc ccatgccgat tcttcgaaag ccatgttgcc     120
agagccaacg tcaagcatct caaaattctc aacactccaa actgtgccct tcagattgta     180
gcccggctga agaacaacaa cagacaagtg tgcattgacc cgaagctaaa gtggattcag     240

| | |
|---|---|
| gagtacctgg agaaagcttt aaacaagggg cgcagagaag aaaaagtggg gaaaaaagaa | 300 |
| aagataggaa aaagaagcg acagaagaag agaaaggctg cccagaaaag gaaaaactag | 360 |

```
<210> SEQ ID NO 3
<211> LENGTH: 282
<212> TYPE: DNA
<213> ORGANISM: Homo sapiens

<400> SEQUENCE: 3
```

| | |
|---|---|
| atgaacgcca aggtcgtggt cgtgctggtc ctcgtgctga ccgcgctctg cctcagcgac | 60 |
| gggaagcccg tcagcctgag ctacagatgc ccatgccgat tcttcgaaag ccatgttgcc | 120 |
| agagccaacg tcaagcatct caaaattctc aacactccaa actgtgccct tcagattgta | 180 |
| gcccggctga gaacaacaa cagacaagtg tgcattgacc cgaagctaaa gtggattcag | 240 |
| gagtacctgg agaaagcttt aaacaagagg ttcaagatgt ga | 282 |

```
<210> SEQ ID NO 4
<211> LENGTH: 270
<212> TYPE: DNA
<213> ORGANISM: Homo sapiens

<400> SEQUENCE: 4
```

| | |
|---|---|
| atgaacgcca aggtcgtggt cgtgctggtc ctcgtgctga ccgcgctctg cctcagcgac | 60 |
| gggaagcccg tcagcctgag ctacagatgc ccatgccgat tcttcgaaag ccatgttgcc | 120 |
| agagccaacg tcaagcatct caaaattctc aacactccaa actgtgccct tcagattgta | 180 |
| gcccggctga gaacaacaa cagacaagtg tgcattgacc cgaagctaaa gtggattcag | 240 |
| gagtacctgg agaaagcttt aaacaagtaa | 270 |

```
<210> SEQ ID NO 5
<211> LENGTH: 282
<212> TYPE: DNA
<213> ORGANISM: Homo sapiens

<400> SEQUENCE: 5
```

| | |
|---|---|
| atgaacgcca aggtcgtggt cgtgctggtc ctcgtgctga ccgcgctctg cctcagcgac | 60 |
| gggaagcccg tcagcctgag ctacagatgc ccatgccgat tcttcgaaag ccatgttgcc | 120 |
| agagccaacg tcaagcatct caaaattctc aacactccaa actgtgccct tcagattgta | 180 |
| gcccggctga gaacaacaa cagacaagtg tgcattgacc cgaagctaaa gtggattcag | 240 |
| gagtacctgg agaaagcttt aaacaagagg ttcaagatgt ga | 282 |

```
<210> SEQ ID NO 6
<211> LENGTH: 360
<212> TYPE: DNA
<213> ORGANISM: Homo sapiens

<400> SEQUENCE: 6
```

| | |
|---|---|
| aagcccgtca gcctgagcta cagatgccca tgccgattct tcgaaagcca tgttgccaga | 60 |
| gccaacgtca agcatctcaa aattctcaac actccaaact gtgcccttca gattgtagcc | 120 |
| cggctgaaga acaacaacag acaagtgtgc attgacccga agctaaagtg gattcaggag | 180 |
| tacctggaga aagctttaaa caacctgatc agcgccgcac cagccgggaa gagggtgatt | 240 |
| gctgggggctc gtgccctgca tccctctcct cccagggcct gccccacagc tcgggccctc | 300 |
| tgtgagatcc gtctttggcc tcctccagaa tggagctggc cctctcctgg ggatgtgtaa | 360 |

```
<210> SEQ ID NO 7
```

<211> LENGTH: 243
<212> TYPE: DNA
<213> ORGANISM: Homo sapiens

<400> SEQUENCE: 7

```
gcccggctga agaacaacaa cagacaagtg tgcattgacc cgaagctaaa gtggattcag      60
gagtacctgg agaaagcttt aaacaacctg atcagcgccg caccagccgg gaagagggtg     120
attgctgggg ctcgtgccct gcatccctct cctcccaggg cctgcccac agctcgggcc      180
ctctgtgaga tccgtctttg gcctcctcca gaatggagct ggccctctcc tggggatgtg     240
taa                                                                   243
```

<210> SEQ ID NO 8
<211> LENGTH: 156
<212> TYPE: DNA
<213> ORGANISM: Homo sapiens

<400> SEQUENCE: 8

```
ctgatcagcg ccgcaccagc cgggaagagg gtgattgctg gggctcgtgc cctgcatccc      60
tctcctccca gggcctgccc cacagctcgg gccctctgtg agatccgtct ttggcctcct     120
ccagaatgga gctggccctc tcctggggat gtgtaa                              156
```

<210> SEQ ID NO 9
<211> LENGTH: 140
<212> TYPE: PRT
<213> ORGANISM: Homo sapiens

<400> SEQUENCE: 9

```
Met Asn Ala Lys Val Val Val Leu Val Leu Val Leu Thr Ala Leu
  1               5                  10                  15

Cys Leu Ser Asp Gly Lys Pro Val Ser Leu Ser Tyr Arg Cys Pro Cys
                 20                  25                  30

Arg Phe Phe Glu Ser His Val Ala Arg Ala Asn Val Lys His Leu Lys
             35                  40                  45

Ile Leu Asn Thr Pro Asn Cys Ala Leu Gln Ile Val Ala Arg Leu Lys
         50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Asn Leu Ile Ser Ala Ala Pro Ala
                 85                  90                  95

Gly Lys Arg Val Ile Ala Gly Ala Arg Ala Leu His Pro Ser Pro Pro
            100                 105                 110

Arg Ala Cys Pro Thr Ala Arg Ala Leu Cys Glu Ile Arg Leu Trp Pro
        115                 120                 125

Pro Pro Glu Trp Ser Trp Pro Ser Pro Gly Asp Val
    130                 135                 140
```

<210> SEQ ID NO 10
<211> LENGTH: 119
<212> TYPE: PRT
<213> ORGANISM: Homo sapiens

<400> SEQUENCE: 10

```
Met Asn Ala Lys Val Val Val Leu Val Leu Val Leu Thr Ala Leu
  1               5                  10                  15

Cys Leu Ser Asp Gly Lys Pro Val Ser Leu Ser Tyr Arg Cys Pro Cys
                 20                  25                  30

Arg Phe Phe Glu Ser His Val Ala Arg Ala Asn Val Lys His Leu Lys
```

```
                    35                  40                  45
Ile Leu Asn Thr Pro Asn Cys Ala Leu Gln Ile Val Ala Arg Leu Lys
         50                  55                  60
Asn Asn Asn Arg Gln Val Cys Ile Asp Pro Lys Leu Lys Trp Ile Gln
 65                  70                  75                  80
Glu Tyr Leu Glu Lys Ala Leu Asn Lys Gly Arg Glu Glu Lys Val
                 85                  90                  95
Gly Lys Lys Glu Lys Ile Gly Lys Lys Arg Gln Lys Arg Lys
            100                 105                 110
Ala Ala Gln Lys Arg Lys Asn
            115
```

<210> SEQ ID NO 11
<211> LENGTH: 93
<212> TYPE: PRT
<213> ORGANISM: Homo sapiens

<400> SEQUENCE: 11

```
Met Asn Ala Lys Val Val Val Leu Val Leu Val Leu Thr Ala Leu
 1               5                  10                  15
Cys Leu Ser Asp Gly Lys Pro Val Ser Leu Ser Tyr Arg Cys Pro Cys
                 20                  25                  30
Arg Phe Phe Glu Ser His Val Ala Arg Ala Asn Val Lys His Leu Lys
             35                  40                  45
Ile Leu Asn Thr Pro Asn Cys Ala Leu Gln Ile Val Ala Arg Leu Lys
         50                  55                  60
Asn Asn Asn Arg Gln Val Cys Ile Asp Pro Lys Leu Lys Trp Ile Gln
 65                  70                  75                  80
Glu Tyr Leu Glu Lys Ala Leu Asn Lys Arg Phe Lys Met
                 85                  90
```

<210> SEQ ID NO 12
<211> LENGTH: 89
<212> TYPE: PRT
<213> ORGANISM: Homo sapiens

<400> SEQUENCE: 12

```
Met Asn Ala Lys Val Val Val Leu Val Leu Val Leu Thr Ala Leu
 1               5                  10                  15
Cys Leu Ser Asp Gly Lys Pro Val Ser Leu Ser Tyr Arg Cys Pro Cys
                 20                  25                  30
Arg Phe Phe Glu Ser His Val Ala Arg Ala Asn Val Lys His Leu Lys
             35                  40                  45
Ile Leu Asn Thr Pro Asn Cys Ala Leu Gln Ile Val Ala Arg Leu Lys
         50                  55                  60
Asn Asn Asn Arg Gln Val Cys Ile Asp Pro Lys Leu Lys Trp Ile Gln
 65                  70                  75                  80
Glu Tyr Leu Glu Lys Ala Leu Asn Lys
                 85
```

<210> SEQ ID NO 13
<211> LENGTH: 92
<212> TYPE: PRT
<213> ORGANISM: Homo sapiens

<400> SEQUENCE: 13

```
Met Asn Ala Lys Val Val Val Leu Val Leu Val Leu Thr Ala Leu
 1               5                  10                  15
```

```
Cys Leu Ser Asp Gly Lys Pro Val Ser Leu Ser Tyr Arg Cys Pro Cys
             20                  25                  30

Arg Phe Phe Glu Ser His Val Ala Arg Ala Asn Val Lys His Leu Lys
         35                  40                  45

Ile Leu Asn Thr Pro Asn Cys Ala Leu Gln Ile Val Ala Arg Leu Lys
 50                  55                  60

Asn Asn Asn Arg Gln Val Cys Ile Asp Pro Lys Leu Lys Trp Ile Gln
 65                  70                  75                  80

Glu Tyr Leu Glu Lys Ala Leu Asn Lys Phe Lys Met
                 85                  90

<210> SEQ ID NO 14
<211> LENGTH: 119
<212> TYPE: PRT
<213> ORGANISM: Homo sapiens

<400> SEQUENCE: 14

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
             20                  25                  30

Asn Cys Ala Leu Gln Ile Val Ala Arg Leu Lys Asn Asn Asn Arg Gln
         35                  40                  45

Val Cys Ile Asp Pro Lys Leu Lys Trp Ile Gln Glu Tyr Leu Glu Lys
 50                  55                  60

Ala Leu Asn Asn Leu Ile Ser Ala Ala Pro Ala Gly Lys Arg Val Ile
 65                  70                  75                  80

Ala Gly Ala Arg Ala Leu His Pro Ser Pro Pro Arg Ala Cys Pro Thr
                 85                  90                  95

Ala Arg Ala Leu Cys Glu Ile Arg Leu Trp Pro Pro Glu Trp Ser
             100                 105                 110

Trp Pro Ser Pro Gly Asp Val
        115

<210> SEQ ID NO 15
<211> LENGTH: 80
<212> TYPE: PRT
<213> ORGANISM: Homo sapiens

<400> SEQUENCE: 15

Ala Arg Leu Lys Asn Asn Asn Arg Gln Val Cys Ile Asp Pro Lys Leu
 1               5                  10                  15

Lys Trp Ile Gln Glu Tyr Leu Glu Lys Ala Leu Asn Asn Leu Ile Ser
             20                  25                  30

Ala Ala Pro Ala Gly Lys Arg Val Ile Ala Gly Ala Arg Ala Leu His
         35                  40                  45

Pro Ser Pro Pro Arg Ala Cys Pro Thr Ala Arg Ala Leu Cys Glu Ile
 50                  55                  60

Arg Leu Trp Pro Pro Glu Trp Ser Trp Pro Ser Pro Gly Asp Val
 65                  70                  75                  80

<210> SEQ ID NO 16
<211> LENGTH: 51
<212> TYPE: PRT
<213> ORGANISM: Homo sapiens

<400> SEQUENCE: 16

Leu Ile Ser Ala Ala Pro Ala Gly Lys Arg Val Ile Ala Gly Ala Arg
 1               5                  10                  15
```

```
Ala Leu His Pro Ser Pro Pro Arg Ala Cys Pro Thr Ala Arg Ala Leu
            20                  25                  30

Cys Glu Ile Arg Leu Trp Pro Pro Glu Trp Ser Trp Pro Ser Pro
        35                  40                  45

Gly Asp Val
    50

<210> SEQ ID NO 17
<211> LENGTH: 747
<212> TYPE: DNA
<213> ORGANISM: Homo sapiens

<400> SEQUENCE: 17
actatagaac caggccgcac tttcactctc cgtcagccgc attgcccgct cggcgtccgg      60
cccccgaccc gcgctcgtcc gccgcccgcc ccgcccgccc gccatgaac gccaaggtc      120 gtggtcgtgc tggtcctcgt gctgaccgcg ctctgcctca gcgacgggaa gcccgtcagc     180
ctgagctaca gatgcccatg ccgattcttc gaaagccatg ttgccagagc caacgtcaag     240
catctcaaaa ttctcaacac tccaaactgt gcccttcaga ttgtagcccg gctgaagaac     300
aacaacagac aagtgtgcat tgacccgaag ctaaagtgga ttcaggagta cctggagaaa     360
gctttaaaca acctgatcag cgccgcacca gccgggaaga gggtgattgc tggggctcgt     420
gccctgcatc cctctcctcc cagggcctgc cccacagctc gggccctctg tgagatccgt     480
ctttggcctc ctccagaatg gagctggccc tctcctgggg atgtgtaatg gtcccccctgc     540 ttacccgcaa aagacaagtc tttacagaat caaatgcaat tttaaatctg agagctcgct     600
ttgagtgact gggttttgtg attgcctctg aagcctatgt atgccatgga ggcactaaca     660
aactctgagg tttccgaaat cagaagcgaa aaaatcagtg aataaaccat catcttgcca     720
ctaccccctc ctgaagccac agcaggg                                          747

<210> SEQ ID NO 18
<211> LENGTH: 751
<212> TYPE: DNA
<213> ORGANISM: Homo sapiens

<400> SEQUENCE: 18
tatagaacca gagcgcactt tcactctccg tcagccgcat tgcccgctcg gcgtccggcc      60
cccgacccgc gctcgtccgc cgcccgccc gcccgcccgc gccatgaacg ccaaggtcgt      120
ggtcgtgctg gtcctcgtgc tgaccgcgct gcctcagc gacgggaagc ccgtcagcct     180
gagctacaga tgcccatgcc gattcttcga aagccatgtt gccagagcca acgtcaagca     240
tctcaaaatt ctcaacactc caaactgtgc ccttcagatt gtagcccggc tgaagaacaa     300
caacagacaa gtgtgcattg acccgaagct aaagtggatt caggagtacc tggagaaagc     360
tttaaacaag gggcgcagag aagaaaaagt ggggaaaaaa gaaagatag gaaaaagaa      420 gcgacagaag aagagaaagg ctgcccagaa aaggaaaaac tagttatctg ccacctcgag     480
atggaccaca gttcacttgc tctcggcgct ttgtaaattt gctcgatcct cctccaggac     540 agaccccat gcagactggg caggggctca gacttccgtg ggggagcagt gctttgctgc     600
cctgccagcc acaccggctt ctgtatttat gtgcttttta aggcccttgt tggtctgcta     660
agttatgaag aaagtagttg tgcagagact ggggcggggg tctgtgacgc ggagcctgtg     720
tgctcaggac tctgtccaga atagcctggg a                                     751

<210> SEQ ID NO 19
```

<211> LENGTH: 860
<212> TYPE: DNA
<213> ORGANISM: Homo sapiens

<400> SEQUENCE: 19

```
cgcggccgca gccgcattgc ccgctcggcg tccggccccc gacccgcgct cgtccgcccg     60
cccgcccgcc cgcccgcgcc atgaacgcca aggtcgtggt cgtgctggtc ctcgtgctga    120
ccgcgctctg cctcagcgac gggaagcccg tcagcctgag ctacagatgc ccatgccgat    180
tcttcgaaag ccatgttgcc agagccaacg tcaagcatct caaaattctc aacactccaa    240
actgtgccct tcagattgta gcccggctga agaacaacaa cagacaagtg tgcattgacc    300
cgaagctaaa gtggattcag gagtacctgg agaaagcttt aaacaagagg ttcaagatgt    360
gagagggtca gacgcctgag gaacccttac agtaggagtc cagctctgaa accagtgtta    420
gggaagggcc tgccacagcc tcccctgcca gggcagggcc ccaggcattg ccaagggctt    480
tgttttggac actttgccat attttcacca tttgattatg tagcaaaata catgacattt    540
attttcatt tagtttgatt attcagtgtc actggcgaca cgtagcagct tagactaagg    600
ccattattgt acttgcctta ttagagtgtc tttccacgga gccactcctc tgactcaggg    660
ctcctgggtt ttggattctc tgagctgtgc aggtggggag actgggctga gggagcctgg    720
ccccatggtc agccctaggg tggagagcca ccaagaggga cgcctggggg tgtcaggacc    780
agtcaacctg ggcaaagcct agtgaaggct tctctctgtg ggatgggatg gtggagggcc    840
acatgggagg ttcaccccct                                                860
```

<210> SEQ ID NO 20
<211> LENGTH: 849
<212> TYPE: DNA
<213> ORGANISM: Homo sapiens

<400> SEQUENCE: 20

```
tctccgtcag ccgcattgcc cgctcggcgt ccggccccg acccgtgctc gtccgcccgc     60
ccgcccgccc gccgcgcca tgaacgccaa ggtcgtggtc gtgctggtcc tcgtgctgac    120
cgcgctctgc ctcagcgacg ggaagcccgt cagcctgagc tacagatgcc catgccgatt    180
cttcgaaagc catgttgcca gagccaacgt caagcatctc aaaattctca acactccaaa    240
ctgtgccctt cagattgtag cccggctgaa gaacaacaac agacaagtgt gcattgaccc    300
gaagctaaag tggattcagg agtacctgga gaaagctta aacaagtaag cacaacagcc    360
aaaaaggact ttccgctaga cccactcgag gaaaactaaa accttgtgag agatgaaagg    420
gcaaagacgt gggggagggg gccttaacca tgaggaccag gtgtgtgtgt ggggtgggca    480
cattgatctg ggatcgggcc tgaggtttgc agcatttaga ccctgcattt atagcatacg    540
gtatgatatt gcagcttata ttcatccatg ccctgtacct gtgcacgttg aacttttat     600
tactgggtt tttctaagaa agaaattgta ttatcaacag cattttcaag cagttagttc     660
cttcatgatc atcacaatca tcatcattct cattctcatt ttttaaatca acgagtactt    720
caagatctga atttggcttg tttggagcat ctcctctgct cccctgggga gtctgggcac    780
agtcaggtgg tggcttaaca gggagctgga aaaagtgtcc tttcttcaga cactgaggct    840
cccgcagca                                                            849
```

<210> SEQ ID NO 21
<211> LENGTH: 859
<212> TYPE: DNA
<213> ORGANISM: Homo sapiens -continued

```
<400> SEQUENCE: 21
tctccgtcag ccgcattgcc cgctcggcgt ccggcccccg acccgtgctc gtccgcccgc    60
ccgcccgccc gcccgcgcca tgaacgccaa ggtcgtggtc gtgctggtcc tcgtgctgac   120
cgcgctctgc ctcagcgacg ggaagcccgt cagcctgagc tacagatgcc catgccgatt   180
cttcgaaagc catgttgcca agccaacgt caagcatctc aaaattctca acactccaaa    240
ctgtgccctt cagattgtag cccggctgaa gaacaacaac agacaagtgt gcattgaccc   300
gaagctaaag tggattcagg agtacctgga gaaagcttta acaagaggt tcaagatgtg    360 agagggtcag acgcctgagg aacccttaca gtaggagccc agctctgaaa ccagtgttag   420
ggaagggcct gccacagcct cccctgccag ggcagggccc caggcattgc caagggcttt   480
gttttgcaca ctttgccata ttttcaccat ttgattatgt agcaaaatac atgacattta   540
tttttcattt agtttgatta ttcagtgtca ctggcgacac gtagcagctt agactaaggc   600
cattattgta cttgccttat tagagtgtct ttccacggag ccactcctct gactcagggc   660
tcctgggttt tgtattctct gagctgtgca ggtggggaga ctgggctgag ggagcctggc   720
cccatggtca gccctagggt ggagagccac caagagggac gcctgggggt gccaggacca   780
gtcaacctgg gcaaagccta gtgaaggctt ctctctgtgg gatgggatgg tggagggcca   840
catgggaggc tcacccccct                                                859

<210> SEQ ID NO 22
<211> LENGTH: 21
<212> TYPE: PRT
<213> ORGANISM: Homo sapiens

<400> SEQUENCE: 22

Ala Leu Cys Glu Ile Arg Leu Trp Pro Pro Glu Trp Ser Trp Pro
 1               5                  10                  15

Ser Pro Gly Asp Val
            20

<210> SEQ ID NO 23
<211> LENGTH: 89
<212> TYPE: PRT
<213> ORGANISM: Homo sapiens

<400> SEQUENCE: 23

Met Asn Ala Lys Val Val Val Val Leu Val Leu Val Leu Thr Ala Leu
 1               5                  10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Asn
                85

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag
```

```
<400> SEQUENCE: 24

His His His His His His
  1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      8x His tag

<400> SEQUENCE: 25

His His His His His His His His
  1               5
```